United States Patent
Nagayama et al.

(10) Patent No.: US 10,245,129 B2
(45) Date of Patent: Apr. 2, 2019

(54) TOOTH BLEACHING DEVICE

(71) Applicant: Panasonic Intellectual Property Management Co., Ltd., Osaka (JP)

(72) Inventors: Masayoshi Nagayama, Osaka (JP); Risa Otsuka, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 12 days.

(21) Appl. No.: 14/895,447

(22) PCT Filed: Jun. 4, 2014

(86) PCT No.: PCT/JP2014/002983
§ 371 (c)(1),
(2) Date: Dec. 2, 2015

(87) PCT Pub. No.: WO2014/196201
PCT Pub. Date: Dec. 11, 2014

(65) Prior Publication Data
US 2016/0135936 A1 May 19, 2016

(30) Foreign Application Priority Data
Jun. 7, 2013 (JP) .................. 2013-120937

(51) Int. Cl.
*A61C 17/00* (2006.01)
*A61C 17/02* (2006.01)
(Continued)

(52) U.S. Cl.
CPC ........ *A61C 17/0211* (2013.01); *A61C 17/022* (2013.01); *A61C 19/066* (2013.01)

(58) Field of Classification Search
CPC ... A61C 17/02; A61C 17/0211; A61C 17/022; A61C 19/063; A61C 19/066
(Continued)

(56) References Cited

U.S. PATENT DOCUMENTS

| 4,164,940 A | * | 8/1979 | Quinby | .................. | A61H 13/00 |
| | | | | | 433/216 |
| 4,865,021 A | * | 9/1989 | Siderman | ............... | A61C 19/06 |
| | | | | | 433/80 |

(Continued)

FOREIGN PATENT DOCUMENTS

| JP | 2005-058486 A | 3/2005 |
| JP | 2008-515575 A | 5/2008 |

(Continued)

OTHER PUBLICATIONS

English Translation of International Preliminary Report on Patentability issued in Application No. PCT/JP2014/002983 dated Dec. 8, 2015.

(Continued)

*Primary Examiner* — Yogesh Patel
*Assistant Examiner* — Gwen M Demosky
(74) *Attorney, Agent, or Firm* — McDermott Will & Emery LLP

(57) ABSTRACT

A tooth bleaching device provided with: a production device that produces an active component for bleaching a tooth; a mouthpiece in which a supply opening, through which the active component produced by the production device is supplied inside the oral cavity, is formed; and a connecting part that connects the production device and the mouthpiece.

18 Claims, 11 Drawing Sheets

(51) Int. Cl.
*A61G 17/02* (2006.01)
*A61C 19/06* (2006.01)
*A61C 17/022* (2006.01)

(58) Field of Classification Search
USPC ............ 433/6, 37, 41–48, 80, 215–216, 229
See application file for complete search history.

(56) References Cited

U.S. PATENT DOCUMENTS

| | | | | |
|---|---|---|---|---|
| 5,104,315 | A * | 4/1992 | McKinley | A61C 17/0211 433/216 |
| 6,893,259 | B1 * | 5/2005 | Reizenson | A61C 17/0211 433/29 |
| 2001/0038993 | A1 * | 11/2001 | Lindquist | A61C 19/063 433/37 |
| 2003/0082500 | A1 | 5/2003 | Lynch | |
| 2005/0037315 | A1 * | 2/2005 | Inoue | A61C 19/063 433/80 |
| 2007/0184404 | A1 * | 8/2007 | Johnki | A61C 17/0211 433/80 |
| 2008/0255498 | A1 * | 10/2008 | Houle | A61C 17/02 604/20 |
| 2009/0004620 | A1 | 1/2009 | Liu et al. | |
| 2009/0208898 | A1 * | 8/2009 | Kaplan | A46B 9/045 433/80 |
| 2011/0027746 | A1 * | 2/2011 | McDonough | A61C 17/0211 433/80 |
| 2011/0076636 | A1 * | 3/2011 | Wolff | A61C 19/063 433/27 |
| 2011/0104631 | A1 * | 5/2011 | Levine | A61C 19/063 433/29 |
| 2011/0183284 | A1 | 7/2011 | Yamanaka et al. | |
| 2012/0015322 | A1 | 1/2012 | Lloyd et al. | |
| 2012/0021375 | A1 * | 1/2012 | Binner | A61B 5/097 433/89 |
| 2012/0040308 | A1 * | 2/2012 | Holbeche | A61C 1/0015 433/89 |
| 2012/0094250 | A1 * | 4/2012 | Lloyd | A61C 19/06 433/80 |
| 2012/0219926 | A1 * | 8/2012 | Sullivan | A61C 17/0211 433/80 |
| 2013/0052613 | A1 * | 2/2013 | Chetiar | A61C 19/066 433/216 |
| 2013/0062014 | A1 | 3/2013 | Koo et al. | |
| 2013/0122457 | A1 * | 5/2013 | Krebber | A61C 19/063 433/82 |
| 2013/0164705 | A1 * | 6/2013 | Tanaka | A61C 17/02 433/82 |
| 2013/0260332 | A1 * | 10/2013 | Shapiro | A61C 17/0211 433/80 |
| 2014/0227657 | A1 * | 8/2014 | Sanders | A61C 19/066 433/32 |
| 2016/0271415 | A1 * | 9/2016 | Min | A61C 19/066 |

FOREIGN PATENT DOCUMENTS

| | | |
|---|---|---|
| JP | 2012-513455 A | 6/2012 |
| WO | 2010/008062 A1 | 1/2010 |
| WO | 2010/103263 A1 | 9/2010 |
| WO | 2011/123124 A1 | 10/2011 |
| WO | 2012/035775 A1 | 3/2012 |
| WO | WO 2013039906 A1 * | 3/2013 ........... A61C 19/066 |

OTHER PUBLICATIONS

International Search Report issued in International Application No. PCT/JP2014/002983 dated Aug. 26, 2014, with English translation.

* cited by examiner

TOOTH BLEACHING DEVICE

RELATED APPLICATIONS

This application is the U.S. National Phase under 35 U.S.C. § 371 of International Application No. PCT/JP2014/002983, filed on Jun. 4, 2014, which in turn claims the benefit of Japanese Application No. 2013-120937, filed on Jun. 7, 2013, the disclosures of which are incorporated by reference herein.

TECHNICAL FIELD

The present invention relates to a teeth whitening device that supplies teeth-whitening active ingredients to teeth.

BACKGROUND ART

A teeth whitening device generates radicals that act on the pigment molecules of teeth and supplies the radicals to the teeth to whiten the teeth. For example, a dentist uses a medical teeth whitening device. The medical teeth whitening device irradiates oxygen bleach with ultraviolet rays or heats oxygen bleach to generate radical species from the oxygen bleach. The ultraviolet ray irradiation or heating is performed while supplying oxygen bleach into the oral cavity. Thus, irradiation of ultraviolet rays or heating may damage the teeth or gum.

A home-use teeth whitening device, which generates radical species without using oxygen bleach, is used in view of such influence on the teeth or gum. For example, Patent Document 1 discloses a teeth whitening device that includes a gas cylinder, which stores gas that generates plasma, a plasma generation cell, which generates plasma containing radical species that are active ingredients from the gas of the gas cylinder, an applicator tube, which includes a plasma discharge port, and a hose, which connects the plasma generation cell and the applicator tube.

The user of the teeth whitening device drives the plasma generation cell while holding the applicator tube so that the plasma discharge port is directed toward the teeth that are subject to whitening. The generated plasma is supplied to the teeth through the applicator tube.

PRIOR ART DOCUMENT

Patent Document

Patent Document 1: Japanese Laid-Open Patent Publication No. 2012-513455

SUMMARY OF THE INVENTION

When using the teeth whitening device of Patent Document 1, the hand of the user holding the applicator tube may move. In such a case, the plasma discharge port of the applicator tube would move away from the teeth that are subject to whitening. This is inconvenient.

It is an object of the present invention to provide a whitening device that is easy to use.

A teeth whitening device according to one embodiment of the present invention includes a generator and a mouthpiece. The generator generates active ingredients for whitening teeth. The mouthpiece includes a supply port that supplies the active ingredients generated by the generator into an oral cavity.

In one embodiment, the mouthpiece includes an outer curved element that guides the active ingredients supplied from the supply port into the mouth along the teeth.

In one embodiment, the mouthpiece includes the supply port formed in a guiding surface that may be opposed to at least either one of upper teeth and lower teeth.

One embodiment of a teeth whitening device further includes a coupling portion that couples the generator and the mouthpiece to each other.

In one embodiment, the mouthpiece includes an inlet-side passage, to which the coupling portion is connected, and an outlet-side passage, which guides gas flowing through the inlet-side passage to the supply port. The outlet-side passage and the inlet-side passage are formed so that a flow speed of gas flowing through the outlet-side passage is lower than a flow speed of gas flowing through the inlet-side passage.

In one embodiment, the mouthpiece includes an occluded element arranged between the upper teeth and the lower teeth.

In one embodiment, the outlet-side passage is formed in the occluded element.

In one embodiment, the supply port is formed in one or both of an upper surface and a lower surface of the occluded element.

In one embodiment, the guiding surface includes a flange projecting from a portion that may be opposed to a gum.

Effect of the Invention

The present invention provides a teeth whitening device that is easy to use.

EMBODIMENTS OF THE INVENTION

First Embodiment

Figure 1:
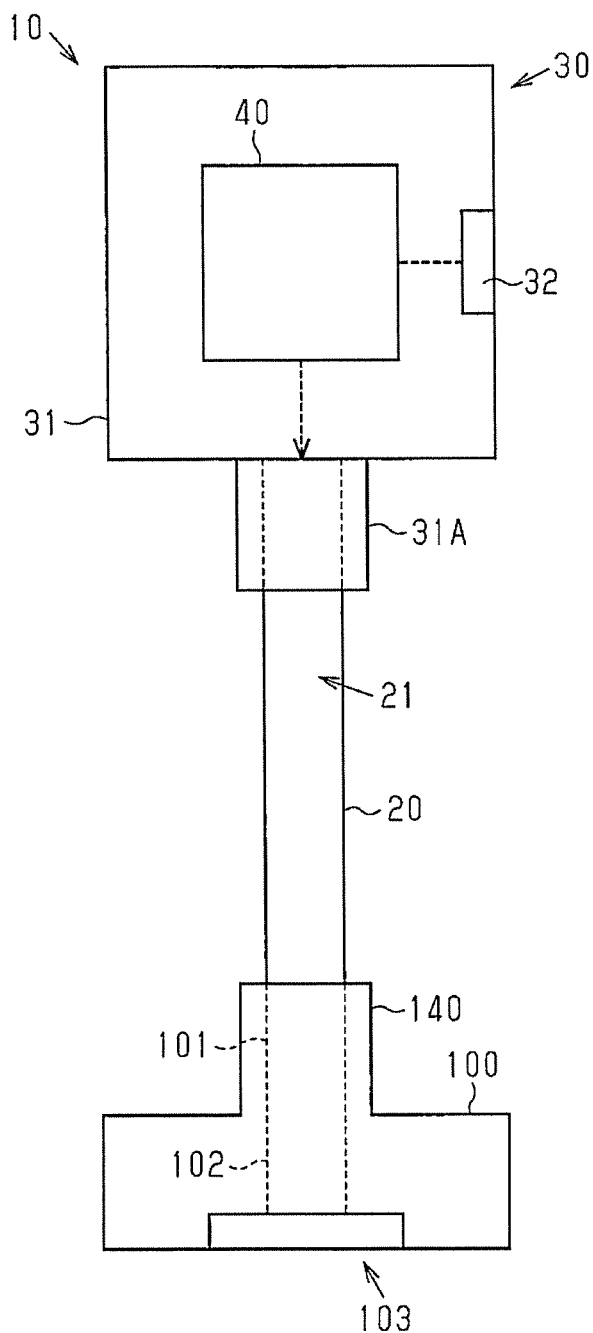
FIG. 1 is a block diagram showing a teeth whitening device of a first embodiment.

The structure of a teeth whitening device 10 will now be described with reference to FIG. 1.

The teeth whitening device 10 includes a generator 30, which generates a teeth whitening fluid that whitens teeth, a mouthpiece 100, which supplies or emits the teeth whitening fluid, and a coupling portion 20, which couples the generator 30 and the mouthpiece 100. One example of a teeth whitening fluid is gas that contains charged microparticle water. Radical species contained in charged microparticle water are one example of teeth-whitening active ingredients.

The generator 30 includes a discharge unit 40, which generates charged microparticle water that contains radical species, a housing 31, which accommodates various components such as the discharge unit 40, and a switch 32, which forms a trigger that generates charged microparticle water in the discharge unit 40. The housing 31 includes a connection portion 31A, to which the coupling portion 20 is connected. The connection portion 31A communicates with the discharge unit 40 and the coupling portion 20.

The mouthpiece 100 includes a connection portion 140, to which the coupling portion 20 is connected, an inlet-side passage 101, which is formed in the connection portion 140, and a supply port 103, which enables communication between the inside of the mouthpiece 100 and the outside of the mouthpiece 100. The mouthpiece 100 further includes an outlet-side passage 102, which guides, to the supply port 103, a teeth whitening fluid that flows through the inlet-side passage 101.

The coupling portion 20 includes a coupling passage 21 that guides a teeth whitening fluid from the generator 30 to the mouthpiece 100. When the coupling portion 20 is inserted into the connection portion 31A of the generator 30, the coupling passage 21 is connected to the outlet of the discharge unit 40. When the coupling portion 20 is inserted into the connection portion 140 of the mouthpiece 100, the coupling passage 21 is connected to the inlet-side passage 101.

The operation of the teeth whitening device 10 will now be described.

A user fits the mouthpiece 100 in his or her oral cavity and closes the mouth to hold the mouthpiece 100. When the switch 32 is turned on, the discharge unit 40 starts to operate and generates a teeth whitening fluid that contains charged microparticle water. The teeth whitening fluid generated by the generator 30 sequentially flows from the generator 30 to the coupling portion 20 and the mouthpiece 100. The teeth whitening fluid in the inlet-side passage 101 of the mouthpiece 100 passes through the outlet-side passage 102 and the supply port 103 and reaches the user's oral cavity. Thus, the charged microparticle water reaches the user's teeth, and the radical species contained in the charged microparticle water reduce electrons from colored organic matters on the teeth. This decomposes the colored organic matters and whitens the teeth.

The teeth whitening device 10 has the advantages described below.

(1) The teeth whitening device 10 includes the generator 30 and the mouthpiece 100. In this structure, the user bites the mouthpiece 100, which is an object that supplies active ingredients to the teeth, to hold the object at a position suitable for whitening his or her teeth. That is, the user can whiten his or her teeth without holding the object that supplies active ingredients to the teeth. Thus, the teeth whitening device 10 is easy to use.

(2) During use of the teeth whitening device 10, the structure of advantage (1) reduces fatigue in the user' hands. This further facilitates the use of the teeth whitening device 10.

(3) The structure of advantage (1) frees the user's hands when using the teeth whitening device 10. Thus, the user can perform other tasks while whitening his or her teeth. This also facilitates the use of the teeth whitening device 10.

(4) In the structure of advantage (1), the supply port 103 is not easily displaced relative to the teeth when the user is using the teeth whitening device 10 as compared with when holding an object that supplies a teeth whitening fluid to teeth with his or her hand. Thus, the teeth whitening fluid supplied from the supply port 103 to the oral cavity is efficiently supplied to the teeth.

(5) The teeth whitening device 10 includes the coupling portion 20. This structure allows the user to fit the mouthpiece 100 in his or her oral cavity even when the generator 30 is separated from the user. This allows the user to be in a relatively free posture when whitening his or her teeth and facilitates the use of the teeth whitening device 10.

Second Embodiment

Figure 2:
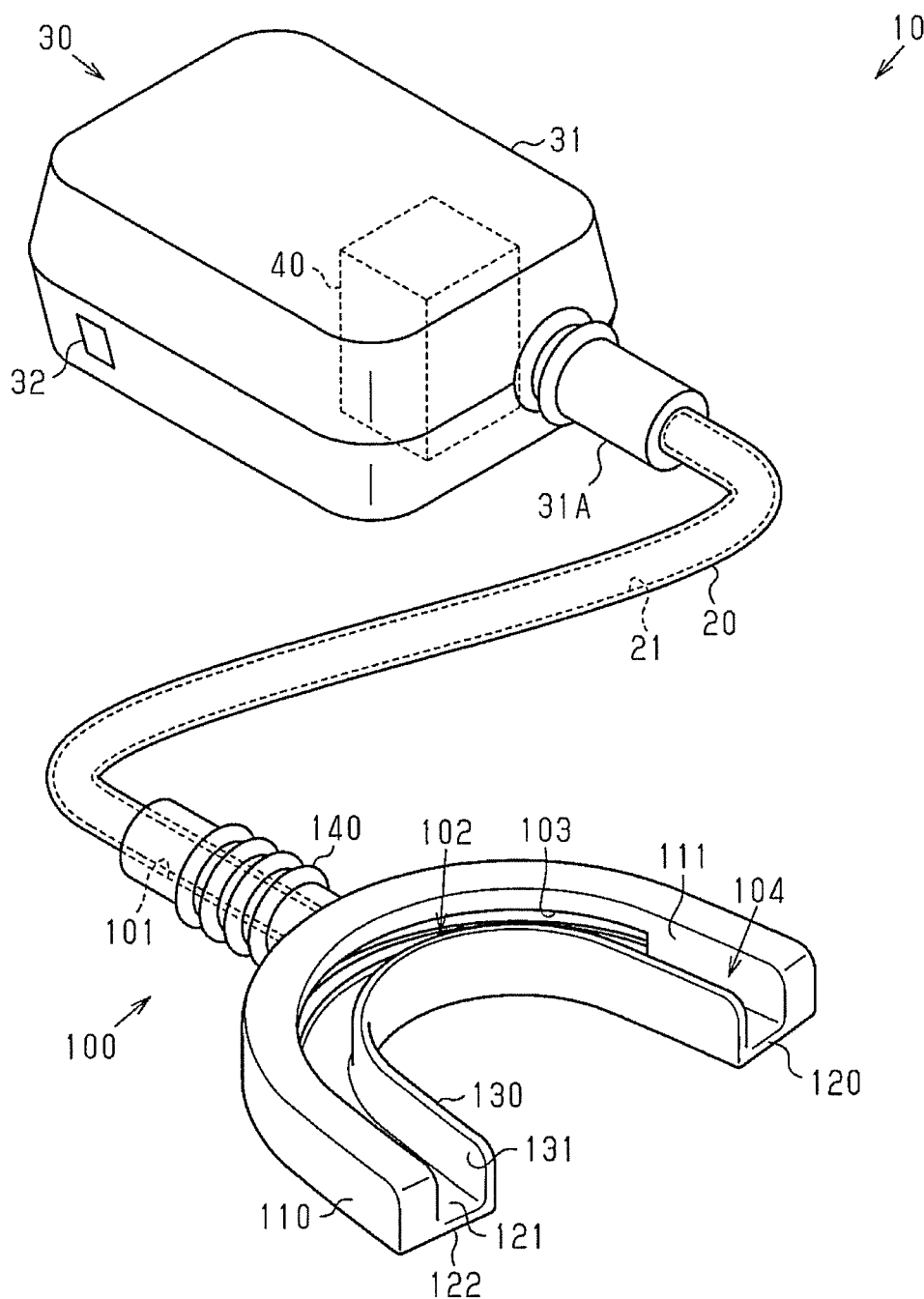
FIG. 2 is a perspective view showing a teeth whitening device of a second embodiment.

The structure of the teeth whitening device 10 will now be described with reference to FIG. 2. The teeth whitening device 10 of a second embodiment includes the following structure, which is not mentioned in the description of the teeth whitening device 10 of the first embodiment.

The generator 30 and the coupling portion 20 include a connection structure that allows the user to select a condition in which the coupling portion 20 is connected to the generator 30 or a condition in which the coupling portion 20 is separated from the generator 30. The mouthpiece 100 and the coupling portion 20 include a connection structure that allows the user to select a condition in which the coupling portion 20 is connected to the mouthpiece 100 or a condition in which the coupling portion 20 is separated from the mouthpiece 100.

One example of the coupling portion 20 is a hose that couples the connection portion 31A of the housing 31 and the connection portion 140 of the mouthpiece 100. The hose is formed from, for example, a resin having high flexibility.

The mouthpiece 100 is formed from, for example, silicone rubber. The mouthpiece 100 includes the connection portion 140, an outer curved element 110, which is curved to guide a teeth whitening fluid, an occluded element 120, which projects from the outer curved element 110, and an inner curved element 130, which projects from the occluded element 120. The occluded element 120 and the inner curved element 130 are curved in conformance with the shape of the outer curved element 110. The mouthpiece 100 further includes a teeth rest 104, which is surrounded by the outer curved element 110, the occluded element 120, and the inner curved element 130.

The outer curved element 110 includes part of the inlet-side passage 101, the outlet-side passage 102, and the supply port 103. The outer curved element 110 further includes a guiding surface 111, which guides the teeth whitening fluid. The supply port 103 opens in the guiding surface 111. In one example, the outlet-side passage 102 and the supply port 103 are formed in the extending direction of the outer curved element 110.

The occluded element 120 projects toward the inner side of the outer curved element 110 and includes an inner surface 121 and an outer surface 122, which are located on relatively opposite sides. The inner curved element 130 projects from the inner surface 121 of the occluded element 120 in the height-wise direction of the mouthpiece 100. The inner curved element 130 includes a guiding surface 131, which opposes the guiding surface 111 of the outer curved element 110.

The operation of the teeth whitening device 10 will now be described.

The user fits the mouthpiece 100 into the oral cavity so that the upper or lower teeth are arranged in the teeth rest 104 of the mouthpiece 100. Then, the user bites the occluded element 120 with the upper and lower teeth to hold the mouthpiece 100. When the mouthpiece 100 is fitted in the oral cavity, the inner surface 121 of the occluded element 120 contacts the upper teeth, and the outer surface 122 of the occluded element 120 contacts the lower teeth.

The teeth whitening fluid generated by the generator 30 sequentially flows from the generator 30 to the coupling portion 20 and the mouthpiece 100. The teeth whitening fluid in the inlet-side passage 101 of the mouthpiece 100 passes through the outlet-side passage 102 and the supply port 103 and reaches the teeth rest 104. The teeth whitening fluid is guided from the teeth rest 104 by the guiding surface 111 of the outer curved element 110 along the teeth and into the teeth rest 104. Thus, the teeth whitening fluid reaches substantially all of the upper and lower teeth and whitens the teeth.

In addition to advantages (1) to (5) of the teeth whitening device 10 of the first embodiment, the teeth whitening device 10 of the second embodiment has the advantages described below.

(6) The mouthpiece 100 includes the outer curved element 110. In this structure, the teeth whitening fluid supplied to the teeth rest 104 is guided by the guiding surface 111 of the outer curved element 110 so that the teeth whitening fluid easily flows along the teeth. Thus, the teeth are whitened more efficiently than when the mouthpiece 100 does not include the outer curved element 110.

(7) The supply port 103 opens in the guiding surface 111 of the outer curved element 110. This structure allows the teeth whitening fluid supplied from the supply port 103 to the oral cavity to easily reach the teeth. Thus, the teeth are whitened more efficiently than when the supply port 103 does not open in the guiding surface 111.

Third Embodiment

Figure 3:
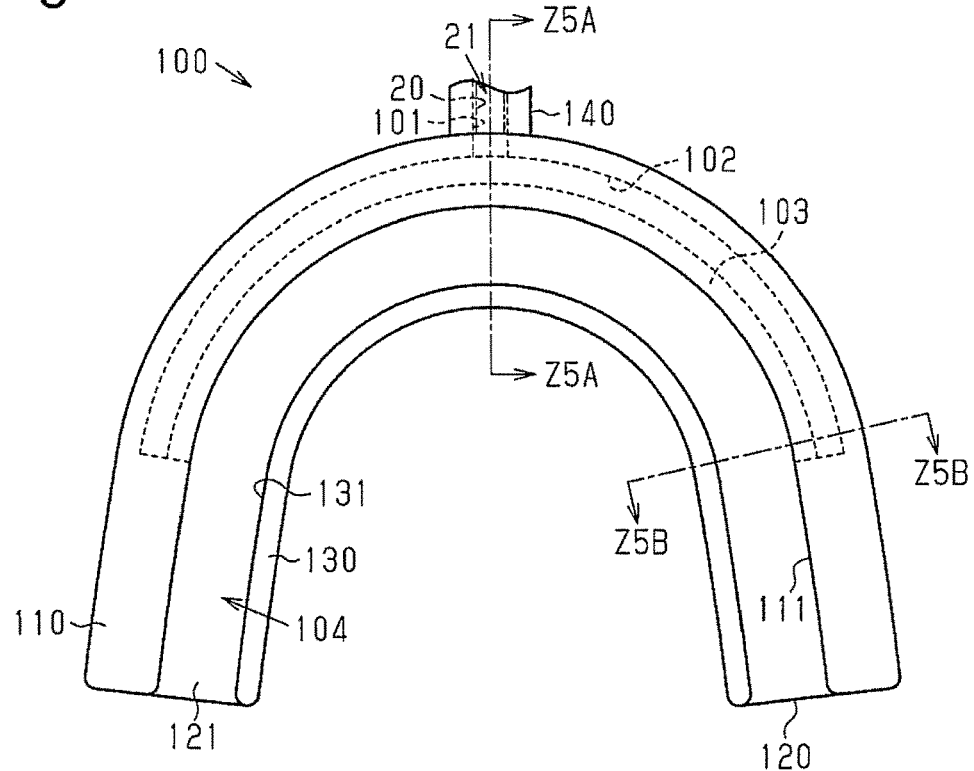
FIG. 3 is a plan view showing a mouthpiece of a third embodiment.

The structure of the teeth whitening device 10 of a third embodiment will now be described with reference to FIG. 3. The teeth whitening device 10 of the third embodiment includes the following structure, which is not mentioned in the description of the teeth whitening device 10 of the second embodiment.

The mouthpiece 100 is symmetrical with respect to, for example, the center line in the sideward direction in a plan view. The mouthpiece 100 may have various sizes depending on, for example, the user's age. The mouthpiece 100 is formed from, for example, silicone rubber. The inlet-side passage 101 is formed in the connection portion 140 and at a base of the connection portion 140 in the outer curved element 110. The outlet-side passage 102 and the supply port 103 are formed in an intermediate portion of the outer curved element 110.

Figure 4:
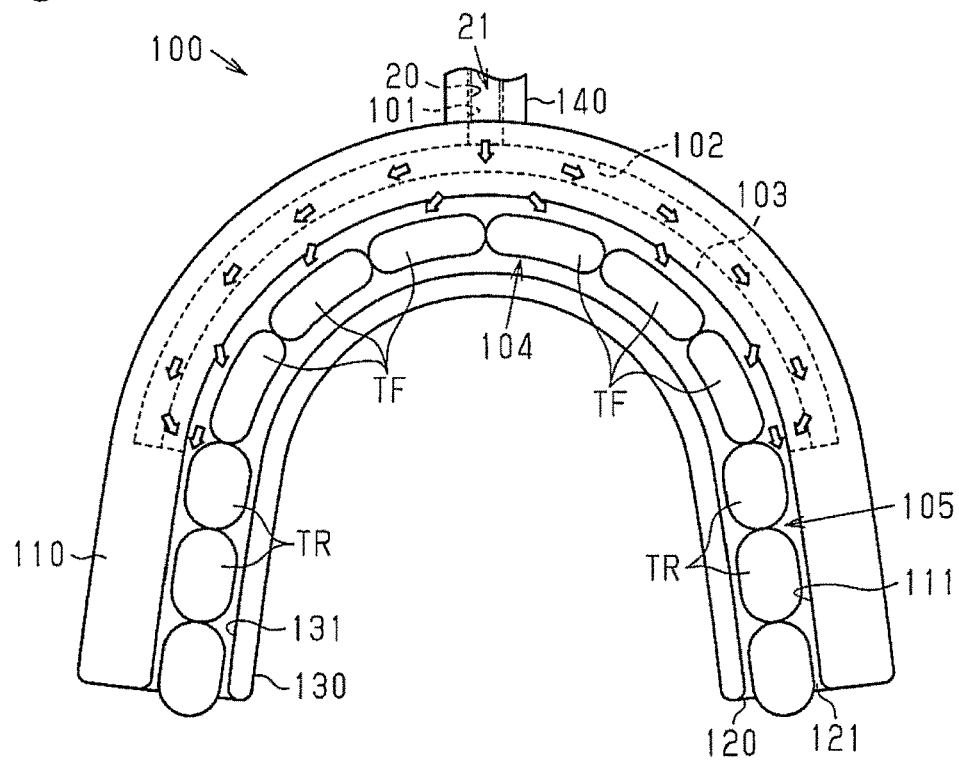
FIG. 4 is a plan view showing a rest of FIG. 3 in which the upper teeth are arranged.

A range in which the outlet-side passage 102 is formed in the outer curved element 110 is set to, for example, a range corresponding to substantially all of the front teeth TF (refer to FIG. 4). A range in which the supply port 103 is formed in the outer curved element 110 is set to, for example, substantially the same as the range in which the outlet-side passage 102 is formed.

The operation of the teeth whitening device 10 will now be described with reference to FIG. 4.

The user fits the mouthpiece 100 in the mouth so that the upper or lower teeth are arranged in the teeth rest 104 of the mouthpiece 100. Then, the user bites the occluded element 120 with the upper and lower teeth to hold the mouthpiece 100. When the mouthpiece 100 is fitted in the oral cavity, the guiding surface 111 of the outer curved element 110 is opposed to the front surface of the teeth and spaced apart from the teeth by part of the teeth rest 104, and the guiding surface 131 of the inner curved element 130 is opposed to the rear surface of the teeth and spaced apart from the teeth by part of the teeth rest 104. Further, the inner surface 121 of the occluded element 120 contacts the upper teeth, and the outer surface 122 of the occluded element 120 contacts the lower teeth.

The arrows shown in FIG. 4 roughly represent the flow of the teeth whitening fluid passing through the coupling portion 20 and the mouthpiece 100 and entering the oral cavity and the flow of the teeth whitening fluid that reaches the teeth. The arrows shown in FIGS. 6A, 6B, 10, 11, 13, 16A, and 16B represent a flow that is the same as or similar to the flow of the teeth whitening fluid represented by the arrows of FIG. 4.

The teeth whitening fluid generated by the generator 30 sequentially flows from the generator 30 to the coupling portion 20 and the mouthpiece 100. The teeth whitening fluid in the inlet-side passage 101 of the mouthpiece 100 passes through the outlet-side passage 102 and the supply port 103 and reaches the teeth rest 104. Thus, the teeth whitening fluid supplied to the teeth rest 104 reaches the front teeth TF or the rear teeth TR and whitens the teeth.

In addition to advantages (1) to (7) of the teeth whitening device 10 of the second embodiment, the teeth whitening device 10 of the third embodiment has the advantage described below.

(8) The supply port 103 is formed to correspond to substantially all of the front teeth TF. This limits the difference in the amount of active gradients distributed to the front teeth TF and reduces differences in the degree of whitening between each of the front teeth TF.

Fourth Embodiment

Figure 5A:
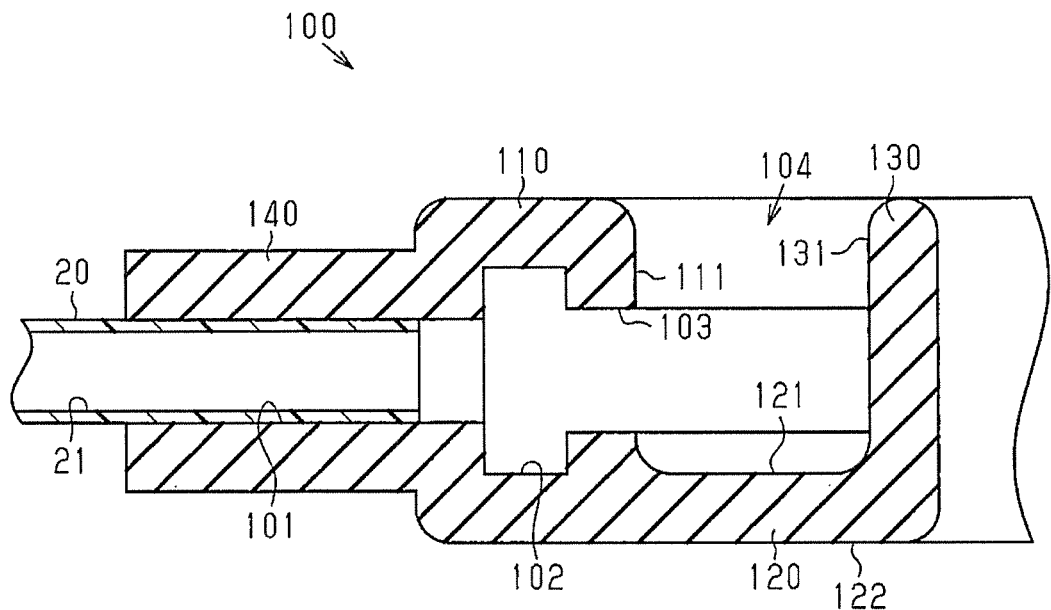
FIG. 5A is a cross-sectional view taken along line Z5A-Z5A of FIG. 3 in a fourth embodiment.
Figure 5B:
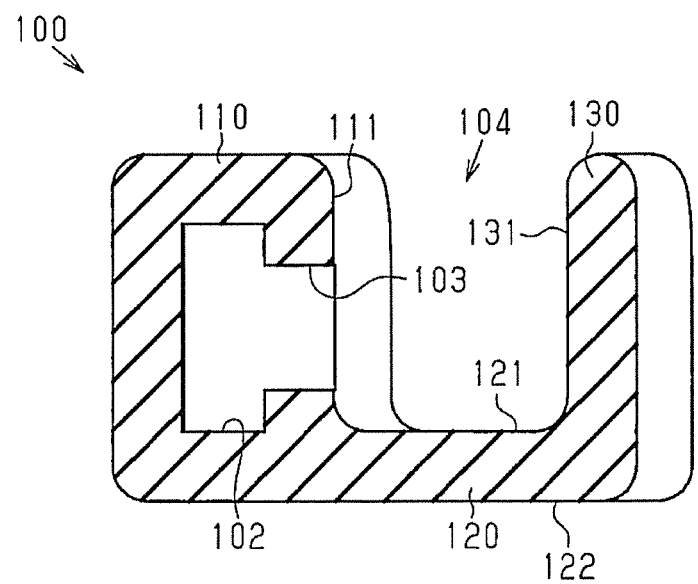
FIG. 5B is a cross-sectional view taken along line Z5B-Z5B of FIG. 3 in the fourth embodiment.

The structure of the teeth whitening device 10 of a fourth embodiment will now be described with reference to, for example, FIGS. 5A and 5B. The teeth whitening device 10 of the fourth embodiment includes the following structure, which is not mentioned in the description of the teeth whitening device 10 of the third embodiment.

In the illustrated example, the size of each portion of the mouthpiece 100 is set as follows. The flow passage area of the outlet-side passage 102 is larger than that of the inlet-side passage 101. Thus, the flow passage area of the outlet-side passage 102 is larger than that of the coupling passage 21, which is overlapped with the inlet-side passage 101.

The size of the outlet-side passage 102 in the height-wise direction of the mouthpiece 100 is larger than the size of the supply port 103 in the height-wise direction of the mouthpiece 100. Further, the size of the outlet-side passage 102 is larger than the size of the inlet-side passage 101 in the height-wise direction of the mouthpiece 100. The size of the supply port 103 is larger than the size of the inlet-side passage 101.

Figure 6A:
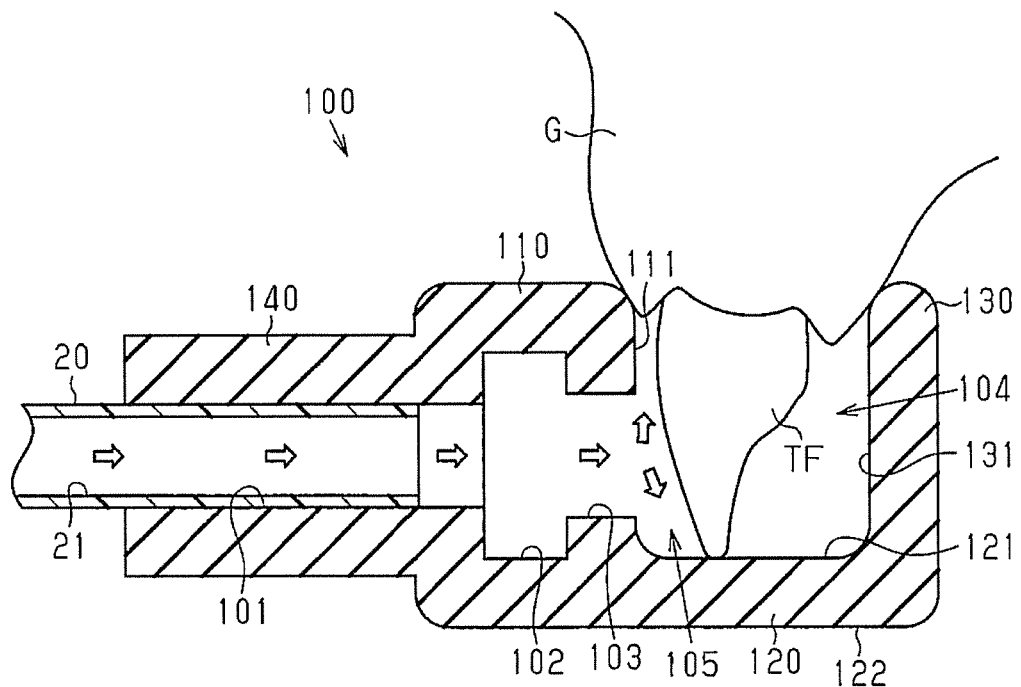
FIG. 6A is a cross-sectional view of front teeth arranged in a teeth rest shown in FIG. 5A.
Figure 6B:
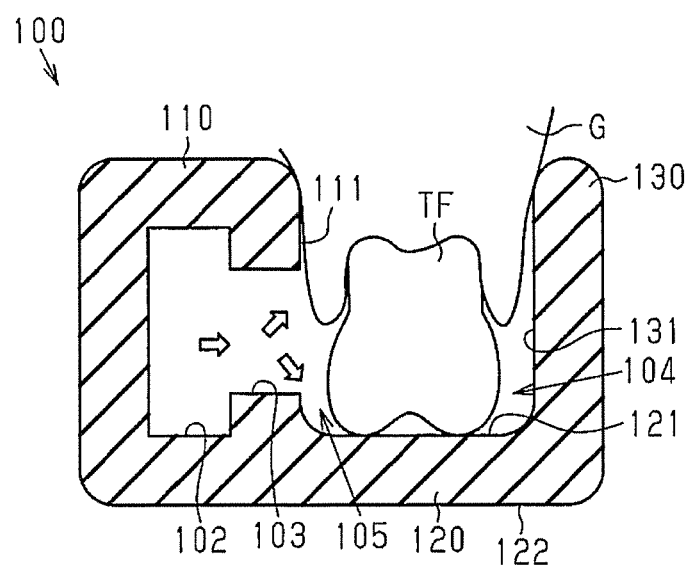
FIG. 6B is a cross-sectional view of rear teeth arranged in a teeth rest shown in FIG. 5B.

FIG. 6A shows the front teeth TF and the surrounding of the front teeth TF when the mouthpiece 100 is fitted in the user's oral cavity. FIG. 6B shows the rear teeth TR and the surrounding of the rear teeth TR when the mouthpiece 100 is fitted in the user's oral cavity.

In one example, the height of the teeth rest 104 is set so that the gum G, where the roots of the front teeth TF and the rear teeth TR are located, is accommodated in the teeth rest 104. The height of the teeth rest 104 is the distance from the inner surface 121 of the occluded element 120 to the top surface of the outer curved element 110 or the top surface of the inner curved element 130.

In one example, the width of the teeth rest 104 is set so as to form a guiding passage 105, which is the gap extending from the guiding surface 111 of the outer curved element 110 to the front teeth TF and the rear teeth TR. The width of the teeth rest 104 is the distance from the guiding surface 111 of the outer curved element 110 to the guiding surface 131 of the inner curved element 130 in the direction the occluded element 120 projects from the guiding surface 111.

In one example, the width of the opening of the teeth rest 104 is set so that the guiding surface 111 of the outer curved element 110 and the guiding surface 131 of the inner curved element 130 contact the gum G, where the roots of the front teeth TF and the rear teeth TR are located, with a suitable pressure. In the illustrated example, the width of the opening of the teeth rest 104 is set to be the same as the width of the teeth rest 104.

As shown in FIG. 6A, when the mouthpiece 100 is fitted in the oral cavity, the incisal edges of the upper front teeth TF contact the inner surface 121 of the occluded element 120, and the incisal edges of the lower front teeth (not shown) contact the outer surface 122 of the occluded element 120. The guiding surface 111 of the outer curved element 110 forms the guiding passage 105 with the front teeth TF. The guiding surface 111 of the outer curved element 110 is in close contact with the front surface of the upper gum G where the roots of the front teeth TF are located. The guiding surface 131 of the inner curved element 130 is in close contact with the rear surface of the upper gum G where the roots of the front teeth TF are located.

As shown in FIG. 6B, when the mouthpiece 100 is fitted in the oral cavity, the occlusion surface of the upper rear teeth TR contact the inner surface 121 of the occluded element 120, and the occlusion surface of the lower rear teeth (not shown) contact the outer surface 122 of the occluded element 120. The guiding surface 111 of the outer curved element 110 forms the guiding passage 105 with the rear teeth TR. The guiding surface 111 of the outer curved element 110 is in close contact with the front surface of the upper gum G where the roots of the rear teeth TR are located. The guiding surface 131 of the inner curved element 130 is in close contact with the rear surface of the upper gum G where the roots of the rear teeth TR are located.

The operation of the teeth whitening device 10 will now be described with reference to FIGS. 6A and 6B.

As shown in FIG. 6A, the teeth whitening fluid is supplied from the coupling passage 21 of the coupling portion 20 to the inlet-side passage 101 of the mouthpiece 100. The teeth whitening fluid of the inlet-side passage 101, which passes through intermediate portions of the outlet-side passage 102 and the supply port 103, reaches the guiding passage 105. This allows the teeth whitening fluid to reach the front teeth TF and whiten the front teeth TF.

As shown in FIG. 6B, the teeth whitening fluid of the outlet-side passage 102, which passes through a portion of the guiding passage 105 located toward the end from an intermediate portion of the supply port 103. This allows the teeth whitening fluid to reach the rear teeth TR and whiten the rear teeth TR.

The teeth whitening fluid is guided from the guiding passage 105 by the guiding surface 111 of the outer curved element 110 and flows along the teeth. This allows the teeth whitening fluid to reach substantially all of the upper and lower teeth and whiten the teeth.

In addition to advantages (1) to (8) of the teeth whitening device 10 of the second embodiment, the teeth whitening device 10 of the third embodiment has the advantages described below.

(9) The flow passage area of the outlet-side passage 102 is larger than that of the inlet-side passage 101. In this structure, the speed of the gas flowing in the outlet-side passage 102 is lower than that in the inlet-side passage 101. Thus, gas is apt to remain in the outlet-side passage 102, and the active ingredients existing in the outlet-side passage 102 are easily diffused in the gas. Further, gas, in which the difference in concentration of the active ingredients is small, is supplied from the supply port 103 to the guiding passage 105. This limits differences in the amount of active ingredients distributed to various portions of the same tooth. Thus, this limits differences in the degree of whitening in each portion of the tooth. Further, the difference in the amount of active ingredients distributed to a plurality of teeth is limited. This limits differences in the degree of whitening between the teeth.

(10) The width of the teeth rest 104 is set so as to form the guiding passage 105 between the outer curved element 110 and the front teeth TF or the rear teeth TR. This structure allows the teeth whitening fluid from the supply port 103 to be guided by the guiding passage 105 and flow along the teeth. Thus, differences in the degree of whitening between the teeth are reduced.

(11) In the structure of advantage (10), the supply port 103 is less likely to be blocked by the teeth. Thus, the flow of the teeth whitening fluid flowing from the supply port 103 to the guiding passage 105 is not hindered. This supplies the teeth whitening fluid more efficiently than when the teeth whitening device 10 does not include the structure of advantage (10).

Fifth Embodiment

Figure 7:
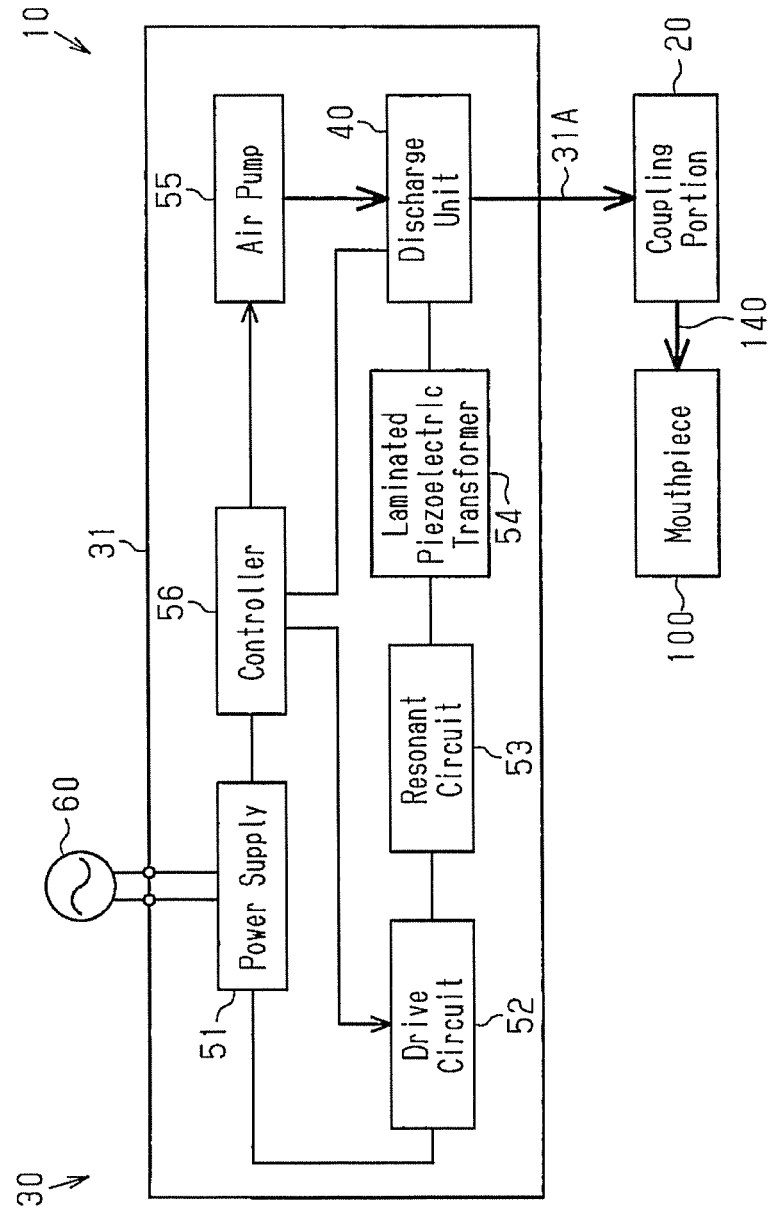
FIG. 7 is a block diagram showing a teeth whitening device of a fifth embodiment.

The structure of the teeth whitening device 10 of a fifth embodiment will now be described with reference to FIG. 7. The teeth whitening device 10 of the fifth embodiment includes the following structure, which is not mentioned in the description of the teeth whitening device 10 of the fourth embodiment.

The generator 30 includes the housing 31, the discharge unit 40, a power supply 51, which rectifies power supplied from a commercial power supply 60, and a drive circuit 52, which changes the frequency of power supplied from the power supply 51 and outputs the changed frequency. The generator 50 also includes a resonant circuit 53, which increases the voltage supplied from the drive circuit 52, and a laminated piezoelectric transformer 54, which converts the voltage supplied from the resonant circuit 53 to high voltage and outputs the high voltage. The generator 50 further includes an air pump 55, which supplies air to the discharge unit 40, and a controller 56, which controls the drive circuit 52, the discharge unit 40, and the air pump 55. The housing 31 accommodates the discharge unit 40, the power supply 51, the drive circuit 52, the resonant circuit 53, the laminated piezoelectric transformer 54, the air pump 55, and the controller 56.

The power supply 51 includes, for example, a diode bridge. The power supply 51 includes a rectification circuit, which performs full-wave rectification on the AC power supplied from the commercial power supply 60, and a capacitor, which eliminates noise from the power rectified by the rectification circuit.

The drive circuit 52 is electrically connected to the power supply 51. The drive circuit 52 includes, for example, a single-phase full-bridge inverter, which includes two arms that are connected in parallel. Each of the two arms includes two metal-oxide-semiconductor field-effect transistors (MOSFETs) that are connected in series. The drive circuit 52 switches on and off the four MOSFETs to generate AC power that has a higher frequency than the AC power supplied from the commercial power supply 60.

The resonant circuit 53, which is, for example, a series LC resonant circuit, includes a circuit configuration in which the drive circuit 52, a reactor, and a primary electrode of the laminated piezoelectric transformer 54 are connected in series. The resonant circuit 53 increases the power supplied from the drive circuit 52 and supplies the power to the laminated piezoelectric transformer 54.

Figure 8:
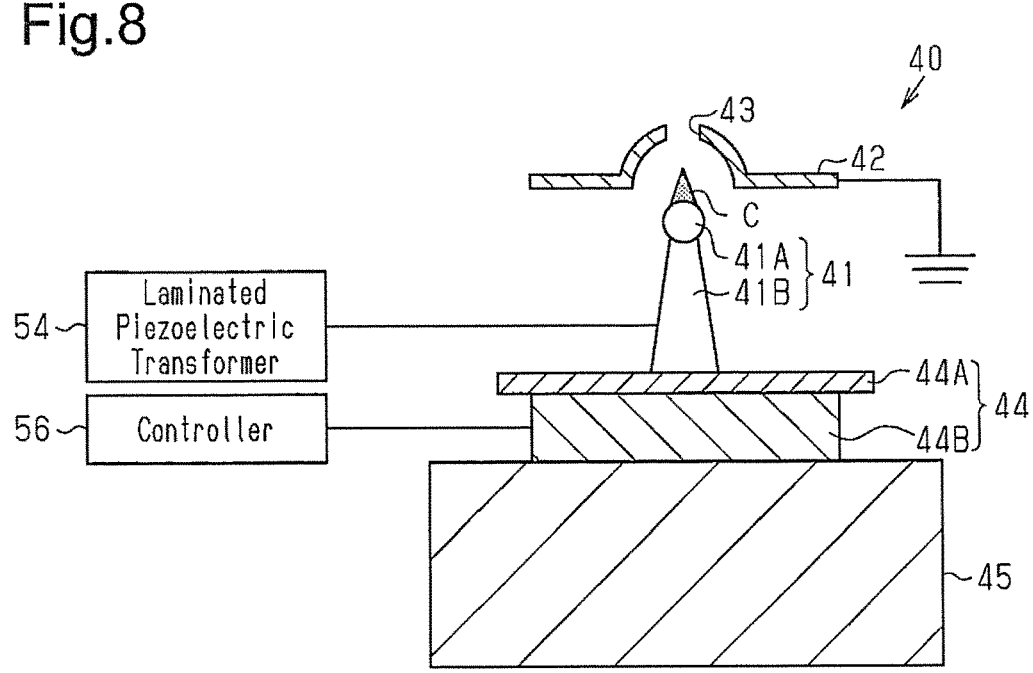
FIG. 8 is a cross-sectional view showing a discharge unit of a sixth embodiment.

The laminated piezoelectric transformer 54 includes the primary electrode, which is electrically connected to the resonant circuit 53, and a secondary electrode, which is electrically connected to an electrode of the discharge unit 40. The laminated piezoelectric transformer 54 transforms the AC power supplied from the resonant circuit 53 and outputs the transformed AC power to the electrode of the discharge unit 40. One example of the electrode of the discharge unit 40 is an atomization electrode 41, which is shown in FIG. 8.

The discharge unit 40 uses the power supplied from the laminated piezoelectric transformer 54 to perform discharging and generates charged microparticle water. The discharging performed by the discharge unit 40 is, for example, corona discharging. The radical species in the charged microparticle water generated from discharging include OH radical species.

The air pump 55 is arranged at a location where air can be supplied to the electrode of the discharge unit 40 and the surrounding of the discharge unit 40. When the air pump 55 is driven, the flow of air passes by the electrode of the discharge unit 40 and the surrounding of the discharge unit 40. The air supplied to the electrode of the discharge unit 40 and to the surrounding of the discharge unit, and the charged microparticle water generated by the discharge unit 40, flow through the outlet of the discharge unit 40 and enter the coupling passage 21 (refer to FIG. 1) of the coupling portion 20.

The controller 56 outputs a control signal to each of the MOSFETs of the drive circuit 52 to control the operation of the drive circuit 52. Further, the controller 56 outputs a control signal to the air pump 55 to control the operation of the air pump 55. The controller 56 starts the operation of the drive circuit 52 and the air pump 55 when, for example, the switch 32 (refer to FIG. 1) of the generator 30 is turned on.

In addition to advantages (1) to (11) of the teeth whitening device 10 of the fourth embodiment, the teeth whitening device 10 of the fifth embodiment has the advantage described below.

(12) The teeth whitening device 10 includes the air pump 55. In this structure, the discharge pressure of the air pump 55 supplies the teeth whitening fluid from the generator 30 to the mouthpiece 100. This forms a suitable flow of the teeth whitening fluid directed from the generator 30 into the oral cavity. Thus, the teeth are whitened more efficiently than when the teeth whitening device 10 does not include the air pump 55.

Sixth Embodiment

The structure of the teeth whitening device 10 of a sixth embodiment will now be described with reference to FIG. 8. The teeth whitening device 10 of the sixth embodiment includes the following structure, which is not mentioned in the description of the teeth whitening device 10 of the fifth embodiment.

FIG. 8 shows one example of a model of the discharge unit 40. The discharge unit 40 includes the atomization electrode 41, which generates charged microparticle water, an opposing electrode 42, which is spaced apart from the atomization electrode 41, a cooling module 44, which cools the atomization electrode 41, and cooling fins 45, which cool the cooling module 44.

The atomization electrode 41 is formed from, for example, metal. The atomization electrode 41 includes a barrel 41B, which is arranged on a cooling insulating plate 44A of the cooling module 44. A distal end of the barrel 41B includes, for example, a spherical head 41A. The barrel 41B has the form of, for example, a truncated cone tapered from the cooling module 44 to the head 41A.

The opposing electrode 42 is formed from, for example, metal. The opposing electrode 42 is grounded. The opposing electrode 42 includes a curved portion that has, for example, a semi-spherical shape. The curved portion includes a discharge port 43, which is in communication with the gap between the atomization electrode 41 and the opposing electrode 42 and with the space outside the opposing electrode 42.

The cooling module 44 includes the cooling insulating plate 44A, which absorbs heat from the atomization electrode 41, and a Peltier module 44B, which cools the cooling insulating plate 44A and the atomization electrode 41. The cooling insulating plate 44A is formed from, for example, a material having high thermal conductance and high withstanding voltage such as alumina. The cooling insulating plate 44A is arranged between the atomization electrode 41 and the Peltier module 44B.

The cooling fins 45 are formed from, for example, a material having high thermal conductance such as alumina. The cooling fins 45 are attached to the Peltier module 44B so that the Peltier module 44B is held between the cooling fins 45 and the cooling insulating plate 44A. Thus, heat is emitted from the Peltier module 44B through the cooling fins 45.

The controller 56 is electrically connected to the Peltier module 44B, which is part of the discharge unit 40, to control the operation of the Peltier module 44B. The Peltier module 44B is operated to cool the atomization electrode 41. Thus, water is collected on the surfaces of the head 41A and the barrel 41B of the atomization electrode 41 and condensed on the atomization electrode 41. When water is condensed on the atomization electrode 41, power is supplied from the laminated piezoelectric transformer 54 to the atomization electrode 41. The water on the surfaces of the head 41A and the barrel 41B of the atomization electrode 41 is gathered on the surface of the head 41A by a Coulomb force. This forms a Taylor cone C on the head 41A.

When the Taylor cone C is formed on the head 41A and discharging occurs between the atomization electrode 41 and the opposing electrode 42, charged microparticle water containing radical species is generated from the Taylor cone C. The charged microparticle water and the air supplied from the air pump 55 (refer to FIG. 7) flow through the discharge port 43 of the opposing electrode 42 to the coupling passage 21 (refer to FIG. 1) of the coupling portion 20.

In addition to advantages (1) to (12) of the teeth whitening device 10 of the fifth embodiment, the teeth whitening device 10 of the sixth embodiment has the advantage described below.

(13) The discharge unit 40 supplies water to the atomization electrode 41 when the cooling module 44 cools the atomization electrode 41. This structure allows the size of the generator 30 to decrease easily as compared with when, for example, water is supplied from a water absorbing tank to the atomization electrode 41.

Seventh Embodiment

Figure 9:
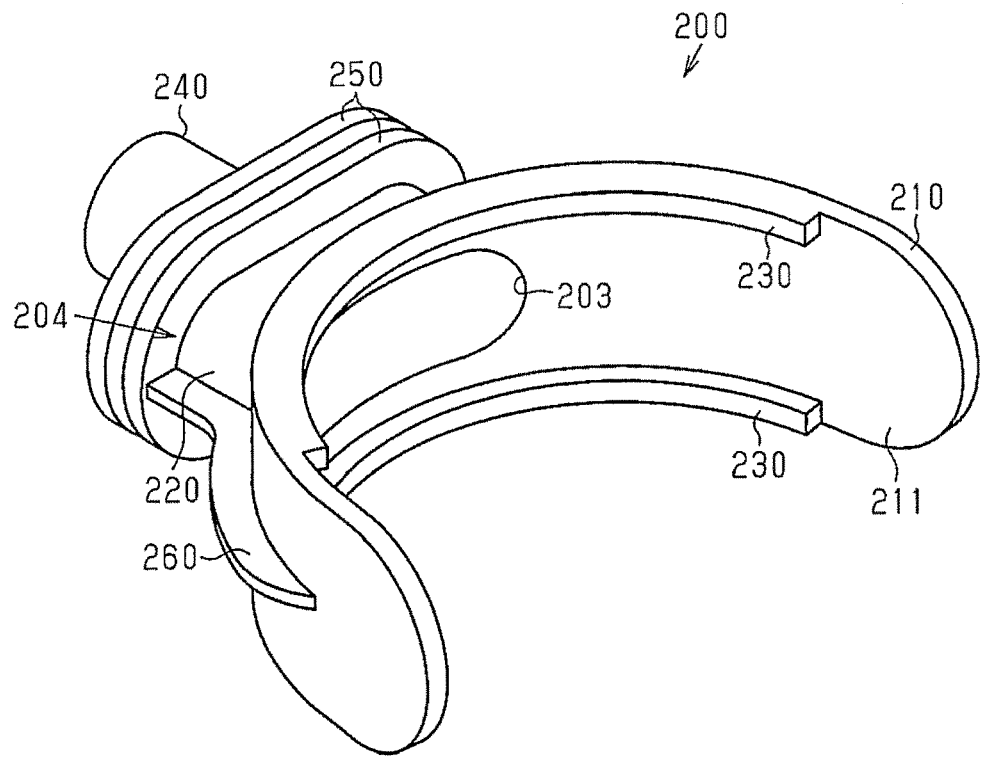
FIG. 9 is a perspective view showing a mouthpiece of a seventh embodiment.

The structure of the teeth whitening device 10 of a seventh embodiment will now be described with reference to FIGS. 9 to 11. Instead of the mouthpiece 100 of the teeth whitening device 10 of the first embodiment, the teeth whitening device 10 of the seventh embodiment includes a mouthpiece 200, which is shown in FIG. 9.

The mouthpiece 200 is symmetrical with respect to, for example, the center line in the sideward direction in plan view. The mouthpiece 200 may have various sizes depending on, for example, the user's age. The mouthpiece 200 is formed from, for example, silicone rubber.

The mouthpiece 200 includes a supply port 203, which enables communication between the inside of the mouthpiece 200 and the outside of the mouthpiece 200. The mouthpiece 200 also includes a connection portion 240, to which the coupling portion 20 (refer to FIG. 2) is connected, an inlet-side passage 201 (refer to FIG. 10), which is formed in the connection portion 240, and a supply port 203, which enables communication between the inside of the mouthpiece 200 and the outside of the mouthpiece 200. The mouthpiece 200 further includes an outlet-side passage 202, which guides, to the supply port 203, a teeth whitening fluid that flows through the inlet-side passage 201.

The mouthpiece 200 further includes an outer curved element 210, which is curved to guide the flow of a teeth whitening fluid, and a hollow barrel 220, which connects the connection portion 240 and the outer curved element 210. In addition, the mouthpiece 200 includes two flanges 230, which project from the outer curved element 210, two rims 250, which project around the barrel 220, and two ribs 260, which are formed between the outer curved element 210 and the rims 250. Each of the flanges 230 is curved in conformance with the shape of the outer curved element 210 and may function as a spacer projection.

The mouthpiece 200 includes an upper lip rest 204 and a lower lip rest 204. The upper lip rest 204 is surrounded by the rear surface of the outer curved element 210, the top surface of the barrel 220, and the side surface of one of the rims 250. The lower lip rest 204 is surrounded by the rear surface of the outer curved element 210, the bottom surface of the barrel 220, and the side surface of the one of the rims 250. In one example, the connection portion 240, the outer curved element 210, the barrel 220, the two flanges 230, the two rims 250, and the two ribs 260 are integrally formed resin elements.

One example of the barrel 220 is an oval tube. As shown in FIG. 10, the outlet-side passage 202 is formed in the barrel 220 and the outer curved element 210. The outer curved element 210 includes a guiding surface 211, which guides the teeth whitening fluid. The supply port 203, which is an opening of the outlet-side passage 202, opens in the guiding surface 211.

The upper flange 230 is formed on the upper edge of the outer curved element 210 and projects toward the inner side of the outer curved element 210. The lower flange 230 is formed on the lower edge of the outer curved element 210 and projects toward the inner side of the outer curved element 210. In another example, which differs from the illustrated one, each flange 230 may include a rounded distal end.

As shown in FIG. 9, the two rims 250 are spaced apart from and opposed to each other along the center axis of the barrel 220. The two ribs 260 extend from the rear surface of the outer curved element 210 to the rims 250 along the rear surface of the outer curved element 210 and the side surface of the barrel 220.

Figure 10:
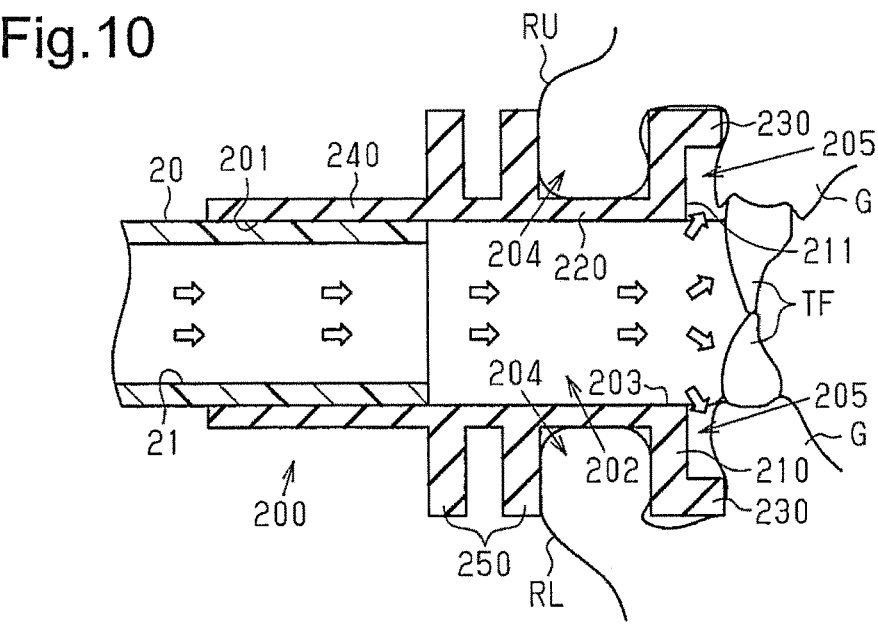
FIG. 10 is a cross-sectional view of the mouthpiece shown in FIG. 9 when used.
Figure 11:
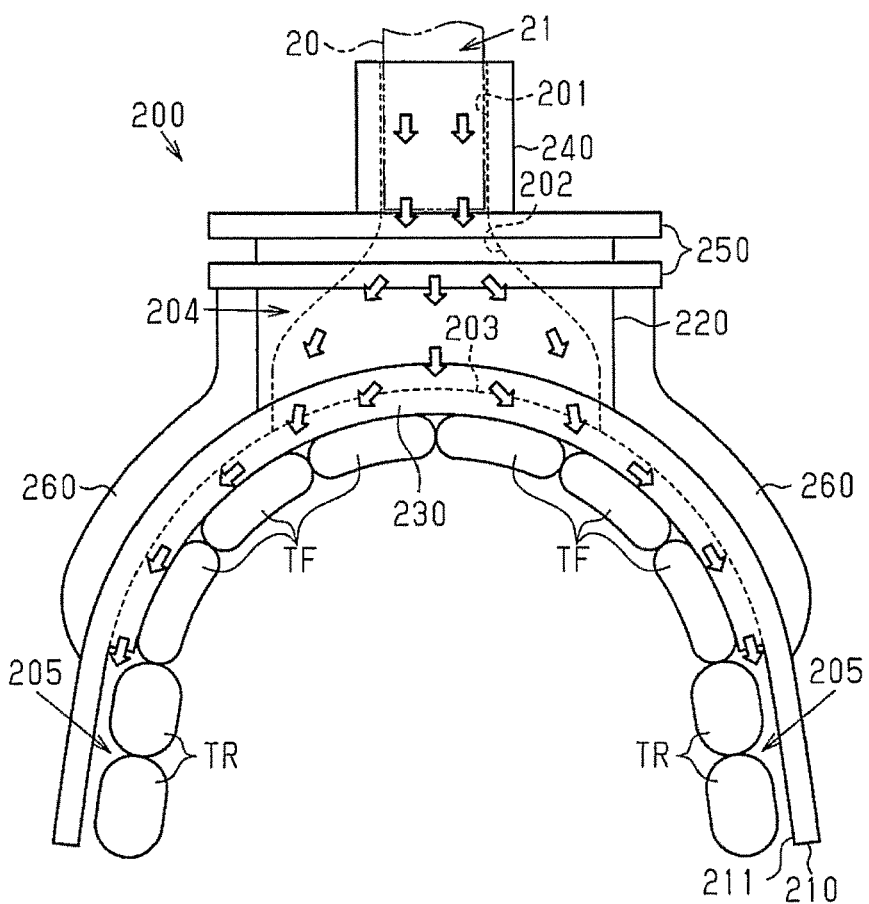
FIG. 11 is a plan view of the mouthpiece shown in FIG. 9 relative to teeth.

FIG. 10 shows the mouthpiece 200 fitted in the user's oral cavity.

The user holds the mouthpiece 200 by arranging the upper lip RU in the upper lip rest 204, the lower lip RL in the lower lip rest 204, the upper flange 230 between the upper lip RU and the gum G, and the lower flange 230 between the lower lip RL and the gum G.

When the mouthpiece 200 is fitted in the oral cavity, the outer curved element 210, the barrel 220, one of the rims 250, and the two ribs 260 each contact the upper lip RU and the lower lip RL. The upper flange 230 contacts the upper gum G so that a guiding passage 205 is formed between the guiding surface 211 of the outer curved element 210 and the upper teeth and the gum G. The lower flange 230 contacts the lower gum G so that the guiding passage 205 is formed between the guiding surface 211 of the outer curved element 210 and the lower teeth and the gum G.

The operation of the teeth whitening device 10 will now be described with reference to FIGS. 10 and 11.

As shown in FIG. 10, the teeth whitening fluid is supplied from the coupling passage 21 of the coupling portion 20 to the outlet-side passage 202 of the mouthpiece 200. The teeth whitening fluid of the outlet-side passage 202 is supplied from the supply port 203 to the guiding passage 205. As shown in FIG. 11, the teeth whitening fluid is guided from the guiding passage 205 by the guiding surface 211 and flows along the teeth. This allows the teeth whitening fluid to reach substantially all of the upper and lower teeth and whiten the teeth.

In addition to advantages (1) to (13) of the teeth whitening device 10 of the sixth embodiment, the teeth whitening device 10 of the seventh embodiment has the advantage described below.

(14) The mouthpiece 200 includes the outer curved element 210, which allows the guiding passage 205 to be formed between the upper teeth and the lower teeth. In this structure, when the user fits the mouthpiece 200 in the oral cavity, the upper teeth and the lower teeth are whitened together. This reduces the time for whitening the teeth as compared with when the mouthpiece 200 does not include the outer curved element 210.

Eighth Embodiment

Figure 12:
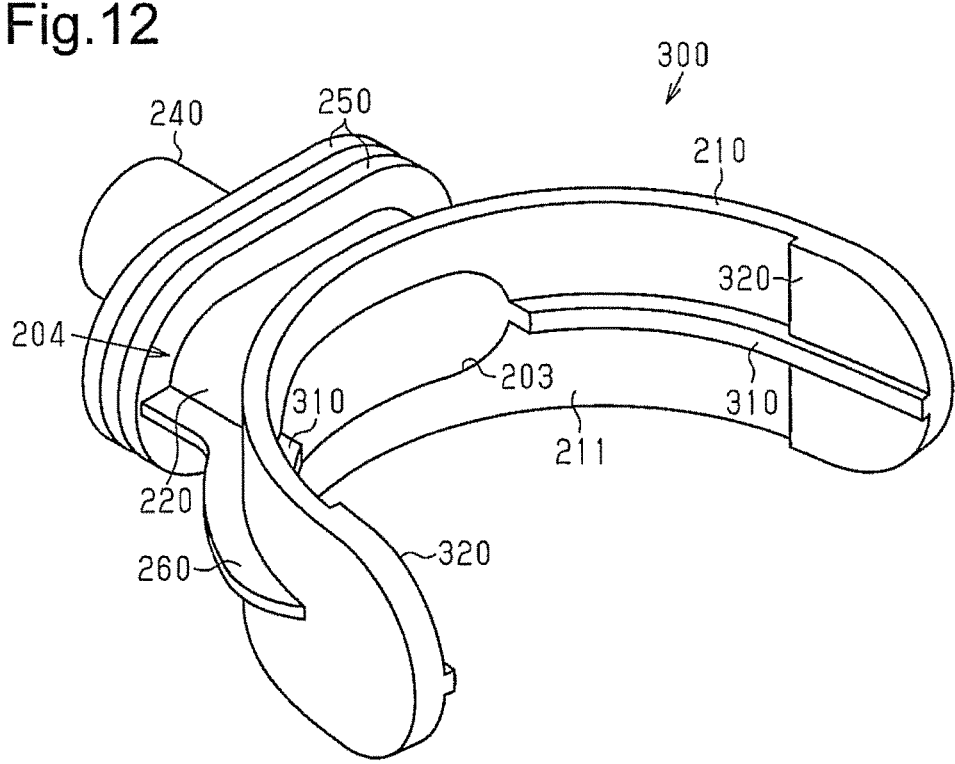
FIG. 12 is a perspective view showing a mouthpiece of an eighth embodiment.

The structure of the teeth whitening device 10 of an eighth embodiment will now be described with reference to FIGS. 12 and 13. Instead of the mouthpiece 100 of the teeth whitening device 10 of the first embodiment, the teeth whitening device 10 of the eighth embodiment includes a mouthpiece 300, which is shown in FIG. 12.

The mouthpiece 300 includes the connection portion 240, the outer curved element 210, the barrel 220, the two rims 250, and the two ribs 260, which are also used in the mouthpiece 200 of the seventh embodiment. Further, the mouthpiece 300 includes the inlet-side passage 201, the outlet-side passage 202, and the supply port 203, which are also used in the mouthpiece 200 of the seventh embodiment. The mouthpiece 300 differs from the mouthpiece 200 of the seventh embodiment as described below.

The mouthpiece 300 includes two occluded elements 310, which project from the outer curved element 210, and two thick portions 320, which project from the outer curved element 210. Each of the occluded elements 310 and each of the thick portions 320 are curved in conformance with the shape of the outer curved element 210.

One occluded element 310 extends from one end of the supply port 203 to one end of the outer curved element 210 and projects toward the inner side of the outer curved element 210 from the guiding surface 211. The other occluded element 310 extends from the other end of the supply port 203 to the other end of the outer curved element 210 and projects toward the inner side of the outer curved element 210 from the guiding surface 211.

One thick portion 320 is formed at one end of the outer curved element 210 and projects toward the inner side of the outer curved element 210 from the guiding surface 211. The other thick portion 320 is formed at the other end of the outer curved element 210 and projects toward the inner side of the outer curved element 210 from the guiding surface 211.

Figure 13:
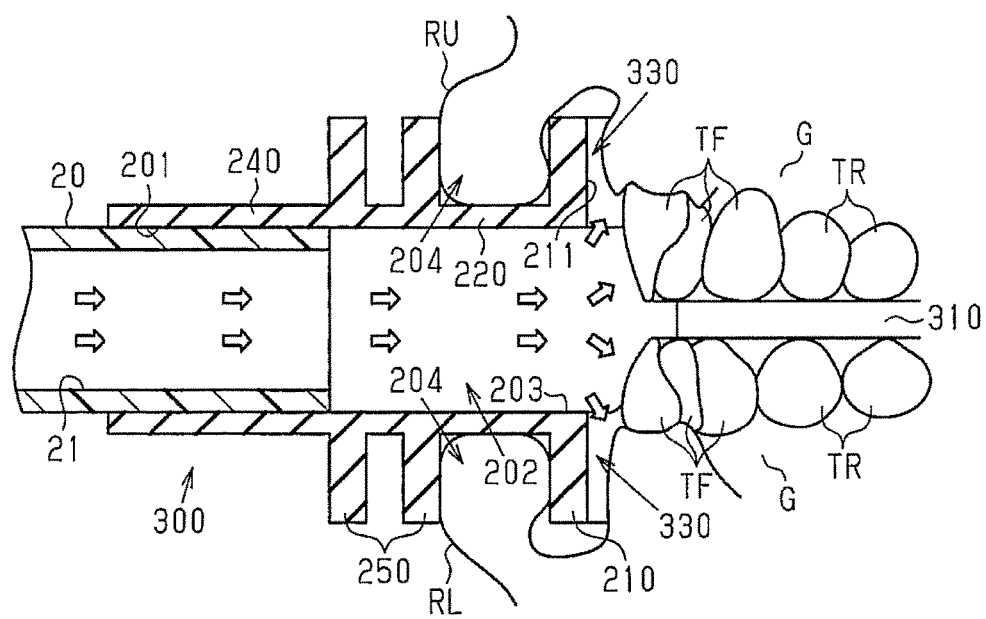
FIG. 13 is a cross-sectional view showing the mouthpiece of FIG. 12 when used.

FIG. 13 shows the mouthpiece 300 fitted in the user's mouth.

The user bites each occluded element 310 with the upper teeth and the lower teeth to hold the mouthpiece 300. When the mouthpiece 300 is fitted in the oral cavity, the guiding surface 211 at the upper side of the occluded element 310 forms a guiding passage 330 between the surface of the upper teeth and the upper gum G. Further, the guiding surface 211 at the lower side of the occluded element 310 forms the guiding passage 330 between the surface of the lower teeth and the lower gum G.

Each thick portion 320 contacts the upper gum G where the roots of a first molar and a second molar are located and the lower gum G where the roots of a first molar and a second molar are located. This ensures the formation of the guiding passage 330.

The operation of the teeth whitening device 10 will now be described with reference to FIG. 13.

The teeth whitening fluid is supplied from the coupling passage 21 of the coupling portion 20 to the outlet-side passage 202 of the mouthpiece 300. The teeth whitening fluid of the outlet-side passage 202 is supplied from the supply port 203 to the guiding passage 330. The teeth whitening fluid is guided from the guiding passage 330 by the guiding surface 211 of the outer curved element 210 and flows along the teeth. This allows the teeth whitening fluid to reach substantially all of the upper and lower teeth and whiten the teeth.

In addition to advantages (1) to (14) of the teeth whitening device 10 of the seventh embodiment, the teeth whitening device 10 of the eighth embodiment has the advantage described below.

(15) The mouthpiece 300 includes the occluded elements 310. In this structure, the occluded elements 310 define the guiding passage 330 between the guiding surface 211 and the upper teeth and the guiding passage 330 between the guiding surface 211 and the lower teeth. This forms a flow of the teeth whitening fluid for the upper teeth and for the lower teeth. Thus, the flow of the teeth whitening fluid along the teeth is more stable than when the mouthpiece 300 does not include the occluded elements 310.

Ninth Embodiment

Figure 14:
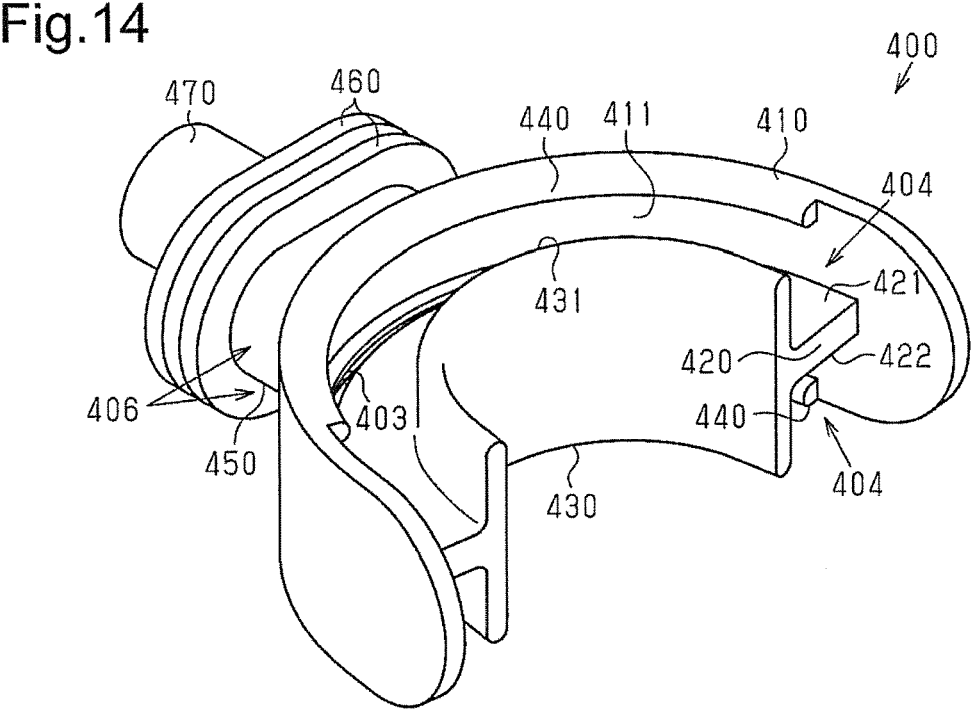
FIG. 14 is a perspective view showing a mouthpiece of a ninth embodiment.

The structure of the teeth whitening device 10 of a ninth embodiment will now be described with reference to FIGS. 14 to 16B. Instead of the mouthpiece 100 of the teeth whitening device 10 of the first embodiment, the teeth whitening device 10 of the ninth embodiment includes a mouthpiece 400, which is shown in FIG. 14.

The mouthpiece 400 is symmetrical with respect to, for example, the center line in the sideward direction in plan view. The mouthpiece 400 may have various sizes depending on, for example, the user's age. The mouthpiece 400 is formed from, for example, silicone rubber.

The mouthpiece 400 includes a connection portion 470, to which the coupling portion 20 (refer to FIG. 15) is connected, an outer curved element 410, which is curved to guide the flow of a teeth whitening fluid, and a hollow barrel 450, which connects the connection portion 470 and the outer curved element 410. Further, the mouthpiece 400 includes two flanges 440, which project from the outer curved element 410, two rims 460, which project around the barrel 450, an occluded element 420, which projects from the outer curved element 410, and an inner curved element 430, which projects from the occluded element 420. One example of the barrel 450 is an oval tube. Each of the flanges 440, the occluded element 420, and the inner curved element 430 are curved in conformance with the shape of the outer curved element 410.

In addition, the mouthpiece 400 includes a teeth rest 404, an upper lip rest 406, and a lower lip rest 406. The teeth rest 404 is surrounded by the outer curved element 410, the occluded element 420, and the inner curved element 430. The upper lip rest 406 is surrounded by the rear surface of the outer curved element 410, the top surface of the barrel 450, and the side surface of one rim 460. The lower lip rest 406 is surrounded by the rear surface of the outer curved element 410, the bottom of the barrel 450, and the side surface of the other rim 460.

Figure 16A:
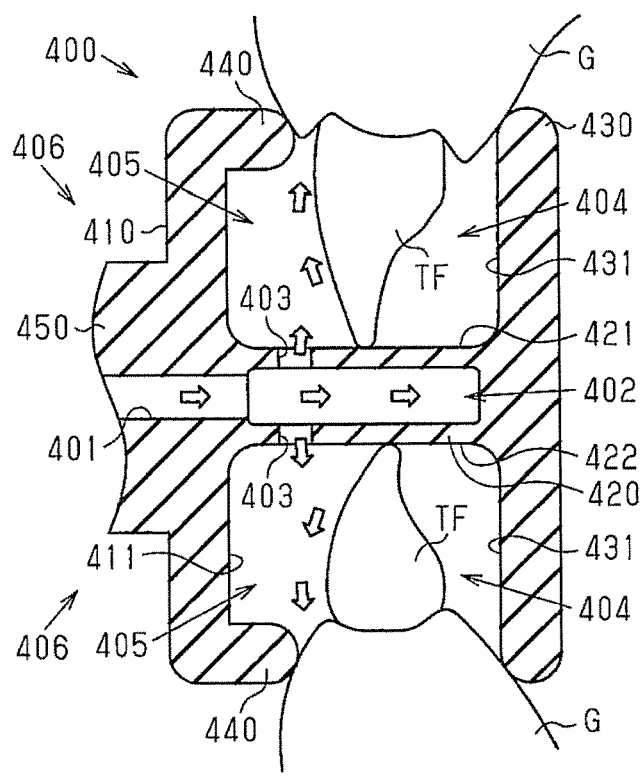
FIG. 16A is a cross-sectional view taken along line Z16A-Z16A shown in FIG. 15.

As shown in FIG. 16A, the mouthpiece 400 further includes an inlet-side passage 401, an outlet-side passage 402, and two supply ports 403. The inlet-side passage 401 is formed in the barrel 450 and the outer curved element 410. The outlet-side passage 402 is formed in the occluded element 420. Each supply port 403 enables communication between the outlet-side passage 402, which is the inside of the mouthpiece 400, and the outside of the mouthpiece 400.

Figure 15:
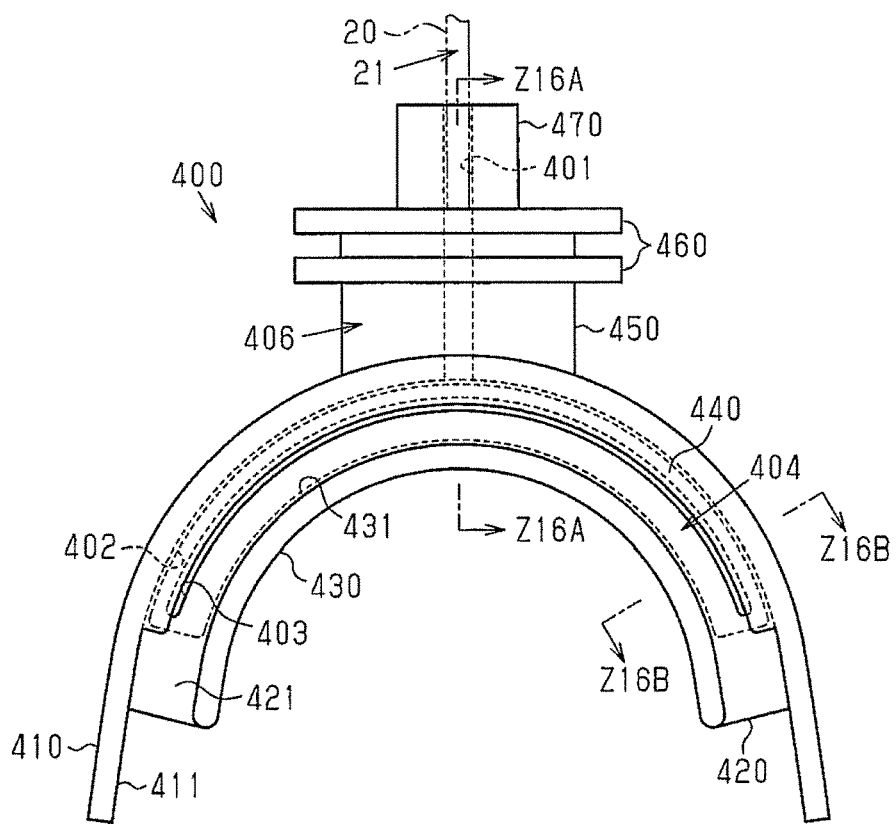
FIG. 15 is a plan view of the mouthpiece shown in FIG. 14.

As shown in FIG. 15, the outlet-side passage 402 and the supply ports 403 are formed in, for example, the extending direction of the occluded element 420. The outer curved element 410 includes a guiding surface 411, which guides a teeth whitening fluid.

As shown in FIG. 14, the upper flange 440 is formed on the upper edge of the outer curved element 410 and projects toward the inner side of the outer curved element 410. The lower flange 440 is formed on the lower edge of the outer curved element 410 and projects toward the inner side of the outer curved element 410. Each flange 440 may include a rounded distal end. The two rims 460 are spaced apart from and opposed to each other along the center axis of the barrel 450.

The occluded element 420 projects toward the inner side of the outer curved element 410 and includes an upper surface 421 and a lower surface 422, which are located at relatively opposite sides. The inner curved element 430 projects from the upper surface 421 of the occluded element 420 in the height-wise direction of the mouthpiece 400. The inner curved element 430 includes a guiding surface 431, which opposes the guiding surface 411 of the outer curved element 410.

Figure 16B:
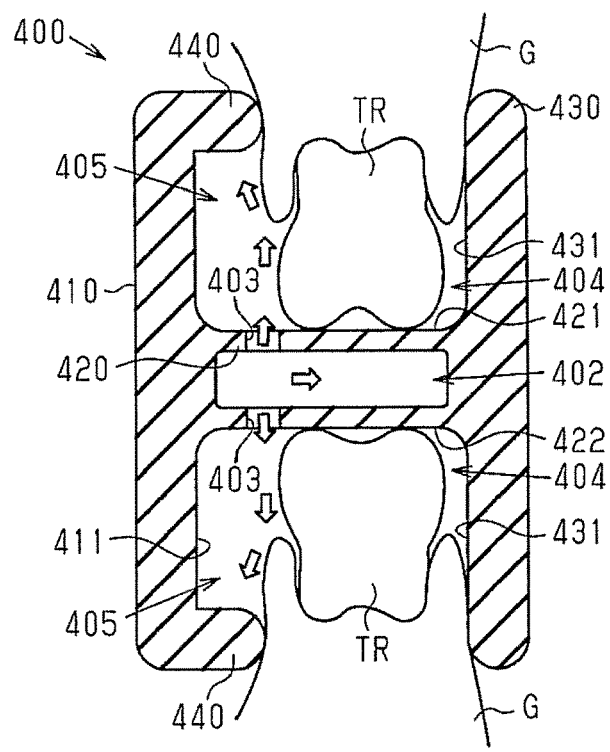
FIG. 16B is a cross-sectional view taken along line Z16B-Z16B shown in FIG. 15.

As shown in FIGS. 16A and 16B, the upper supply port 403 opens in the upper surface 421 of the occluded element 420, and the lower supply port 403 opens in the lower surface 422 of the occluded element 420. The upper supply port 403 and the lower supply port 403 are opposed to each other and spaced apart from the outlet-side passage 402, which is formed in the occluded element 420. The flow passage area of the outlet-side passage 402 is larger than the flow passage area of the coupling passage 21 of the coupling portion 20 (refer to FIG. 15), the flow passage area of the inlet-side passage 401, and the flow passage area of each supply port 403.

The supply ports 403 of the occluded element 420 are located close to the outer curved element 410 in the direction the occluded element 420 projects from the guiding surface 411 of the outer curved element 410.

FIG. 16A shows the front teeth TF and the surrounding of the front teeth TF in the user's oral cavity, in which the mouthpiece 400 is fitted. FIG. 16B shows the rear teeth TR and the surrounding of the rear teeth TR in the user's oral cavity, in which the mouthpiece 400 is fitted.

In one example, the height of the teeth rest 404 is set so that the gum G, where the roots of the front teeth TF and the rear teeth TR are located, is accommodated in the teeth rest 404. The height of the teeth rest 404 is the distance from the upper surface 421 of the occluded element 420 to the top surface of the outer curved element 410 or the top surface of the inner curved element 430.

In one example, the width of the teeth rest 404 is set so as to form a guiding passage 405, which is the gap extending from the guiding surface 411 of the outer curved element 410 to the front teeth TF and the rear teeth TR. The width of the teeth rest 404 is the distance from the guiding surface 411 of the outer curved element 410 to the guiding surface 431 of the inner curved element 430 in the direction the occluded element 420 projects from the guiding surface 411.

In one example, the width of the opening of the teeth rest 404 is set so that the guiding surface 411 of the outer curved element 410 and the guiding surface 431 of the inner curved element 430 contact the gum G, where the front teeth TF and the rear teeth TR, are located, with a suitable pressure. The width of the opening of the teeth rest 404 is the same as the distance from the distal end of the flange 440 to the guiding surface 431 of the inner curved element 430 in the direction the occluded element 420 projects from the guiding surface 411.

As shown in FIG. 16A, when the mouthpiece 400 is fitted in the mouth, the upper lip RU is arranged in the upper lip rest 406, and the lower lip RL is arranged in the lower lip rest 406. Further, the incisal edges of the upper front teeth TF contact the upper surface 421 of the occluded element 420, and the incisal edges of the lower front teeth TF contact the lower surface 422 of the occluded element 420.

The guiding surface 411 of the outer curved element 410 forms the guiding passage 405 with the front teeth TF. The upper flange 440 is in contact with the front surface of the root of the front teeth TF in the upper gum G. The lower flange 440 is in close contact with the front surface of the lower gum G where the roots of the front teeth TF are located. The guiding surface 431 of the inner curved element 430 is in close contact with the rear surface of the upper gum G where the roots of the front teeth TF are located and the rear surface of the lower gum G where the roots of the front teeth TF are located. The rounded portion of each flange 440 softens the contact with the gum G.

As shown in FIG. 16B, when the mouthpiece 400 is fitted in the mouth, the occlusion surface of the upper rear teeth TR contacts the upper surface 421 of the occluded element 420, and the occlusion surface of the lower rear teeth TR contacts the lower surface 422 of the occluded element 420.

The guiding surface 411 of the outer curved element 410 forms the guiding passage 405 with the rear teeth TR. The upper flange 440 is in close contact with the front surface of the upper gum G where the roots of the rear teeth TR are located. The lower flange 440 is in close contact with the front surface of the lower gum G where the roots of the rear teeth TR are located. The guiding surface 431 of the inner curved element 430 is in close contact with the rear surface of the upper gum G where the roots of the rear teeth TR are located and the rear surface of the lower gum G where the roots of the rear teeth TR are located.

The operation of the teeth whitening device 10 will now be described with reference to FIGS. 16A and 16B.

As shown in FIG. 16A, the teeth whitening fluid is supplied from the coupling passage 21 of the coupling portion 20 (refer to FIG. 15) to the inlet-side passage 401 of the mouthpiece 400. The teeth whitening fluid is supplied from the inlet-side passage 401 to the outlet-side passage 402. This reduces the flow speed of the teeth whitening fluid. The teeth whitening fluid of the outlet-side passage 402, which passes through an intermediate portion of the supply port 403, reaches the guiding passage 405. This allows the teeth whitening fluid to reach the front teeth TF and whiten the front teeth TF.

As shown in FIG. 16B, the teeth whitening fluid of the outlet-side passage 402, which passes through a portion of the guiding passage 405 located toward the end from the intermediate portion of the supply port 403. This allows the teeth whitening fluid to reach the rear teeth TR and whiten the rear teeth TR are whitened.

The teeth whitening fluid is guided from the guiding passage 405 by the guiding surface 411 of the outer curved element 410 and flows along the teeth. This allows the teeth whitening fluid to reach substantially all of the upper and lower teeth and whiten the teeth.

In addition to advantages (1) to (6) and (8) to (15) of the teeth whitening device 10 of the eighth embodiment, the teeth whitening device 10 of the ninth embodiment has the advantages described below.

(16) In the mouthpiece 400, the outlet-side passage 402 is formed in the occluded element 420, and the supply port 403 is formed in each of the upper surface 421 and the lower surface 422 of the occluded element 420. This structure greatly changes the flow direction of the teeth whitening fluid in the mouthpiece 400 when flowing through the outlet-side passage 402 and the supply ports 403. Thus, the teeth whitening fluid is apt to remain in the outlet-side passage 402, and the active ingredients existing in the outlet-side passage 402 are easily diffused in the teeth whitening fluid. Further, a teeth whitening fluid, in which the difference in concentration of the active ingredients is small, is supplied from the supply port 403 to the guiding passage 405. Thus, this limits differences in the degree of whitening in each portion of the same tooth and differences in the degree of whitening teeth that differ from each other.

(17) The outlet-side passage 402 is formed in the occluded element 420. In this structure, the thickness of the outer curved element 410 can be reduced to a larger extent than when a passage having the same volume as the outlet-side passage 402 is formed in the outer curved element 410. The reduction in the thickness of the outer curved element 410 allows the user to easily fit the mouthpiece 400 in the oral cavity.

MODIFIED EXAMPLES

The description of each of the above embodiments illustrates an embodiment of the teeth whitening device of the present invention and is not considered to be restrictive. In addition to each of the embodiments, the teeth whitening device of the present invention may include, for example, the following modified examples of each embodiment.

A modified example of the mouthpiece 100 of the first to sixth embodiments is configured to whiten the lower teeth.

In a modified example of the mouthpiece 100 of the second to sixth embodiments, the size of the outlet-side passage 102 is set to be the same as or smaller than that of the supply port 103.

In a modified example of the mouthpiece 100 of the second to sixth embodiments, the supply port 103 is formed so that the supply port 103 opposes only one of the front teeth TF and the rear teeth TR.

In a modified example of the mouthpiece 100 of the second to sixth embodiments, the supply port 103 is formed at a location opposing a particular tooth.

A modified example of the mouthpiece 100 of the second to sixth embodiments includes a plurality of supply ports 103.

In a modified example of the mouthpiece 100 of the second to sixth embodiments, the coupling portion 20 is inserted into the entire inlet-side passage 101. Thus, the gas supplied from the generator 30 to the coupling portion 20 is supplied sequentially from the coupling passage 21, which is overlapped with the inlet-side passage 101, through the outlet-side passage 102 and the supply port 103 to the teeth rest 104.

A modified example of the mouthpiece 100 of the second to sixth embodiments includes two mouthpieces 100 and two coupling portions 20. One mouthpiece 100 is used to whiten the upper teeth, and the other mouthpiece 100 is used to whiten the lower teeth. One mouthpiece 100 is coupled to the generator 30 by one coupling portion 20, and the other mouthpiece 100 is coupled to the generator 30 by the other coupling portion 20. In the teeth whitening device 10 of the modified example, the user fits the two mouthpieces 100 together. This allows the upper teeth and the lower teeth to be whitened together.

The teeth whitening device 10 of a further modified example includes a common coupling portion that couples the two mouthpieces 100 and the generator 30, instead of the two coupling portions 20.

A modified example of the teeth whitening device 10 of the fifth or sixth embodiment includes a manual air pump instead of the electric air pump 55.

A modified example of the generator 30 of the fifth or sixth embodiment includes a primary battery or a rechargeable battery instead of the power supply 51.

A modified example of the resonant circuit 53 of the fifth or sixth embodiment includes a circuit configuration in which a secondary electrode of the laminated piezoelectric transformer 54, a reactor, and the atomization electrode 41 of the discharge unit 40 are connected in series.

A modified example of the discharge unit 40 of the sixth embodiment includes a device that condenses water on the atomization electrode 41 or a device that supplies water to the atomization electrode 41 instead of the cooling module 44.

In a modified example of the mouthpiece 200 of the seventh embodiment, the flanges 230 are closer to the supply port 203 than the edge of the outer curved element 210.

In the modified example of the mouthpiece 200 of the seventh embodiment, one or both of the two flanges 230 are omitted. In another example, one or both of the two rims 250 are omitted. In a further example, the two ribs 260 are omitted.

In a modified example of the mouthpiece 300 of the eighth embodiment, the two occluded elements 310 are omitted.

In a modified example of the mouthpiece 400 of the ninth embodiment, the occluded element 420 includes a plurality of supply ports 403.

In a modified example of the mouthpiece 400 of the ninth embodiment, the lower supply port 403 and a portion that forms the lower teeth rest 404 in the outer curved element 410 and the inner curved element 430 are omitted so that only the upper teeth are whitened.

In a modified example of the mouthpiece 400 of the ninth embodiment, the upper supply port 403 and a portion that forms the upper teeth rest 404 in the outer curved element 410 and the inner curved element 430 are omitted so that only the lower teeth are whitened.

Modified examples of the mouthpieces 100, 200, 300, and 400 of the embodiments are formed from a flexible material other than silicone rubber, such as elastomer rubber, flexible polyvinyl chloride, and ethylene propylene diene rubber.

A modified example of the generator 30 of each embodiment supplies DC power to the discharge unit 40 and uses the power to perform discharging in the discharge unit 40.

A modified example of the generator 30 of each embodiment performs discharging other than corona discharging, for example, glow discharging or arc discharging.

In a modified example of the teeth whitening device 10 of each embodiment, the coupling portion 20 is integrated with at least one of the generator 30 or the mouthpiece (100; 200; 300; 400).

In a modified example of the teeth whitening device 10 of each embodiment, the generator 30 is directly connected to the mouthpiece (100; 200; 300; 400).

A teeth whitening device (10) according to one or more representative embodiments and modified examples includes a generator (30), which generates a teeth whitening fluid when activated, a mouthpiece (100; 200; 300; 400), which is connected to the generator 30 in a fluid-communicable manner, wherein the mouthpieces (100; 200; 300; 400) respectively include U-shaped outer curved elements (110; 210; 410) and supply ports (103; 203; 403) that supply the teeth whitening fluid. In a preferred example, the user can hold the outer curved element with the lips and gum and/or the upper and lower jaws. This allows the user to release his or her hands from the mouthpiece when supplying the teeth whitening fluid from the supply port of the mouthpiece and improves the convenience of the teeth whitening device 10.

The outer curved elements (110; 210; 410) may include curved guiding surfaces (111; 211; 411), which are configured to guide a teeth whitening fluid discharged from the supply ports (103; 203; 403). This may improve one or both of the guiding efficiency and distribution evenness of the teeth whitening fluid.

The supply ports (103; 203) may open in curved guiding surfaces (111; 211), respectively. This may improve the efficiency for supplying a teeth whitening fluid to teeth.

The mouthpieces (100; 400) may respectively include internal hollows (102; 402), which are arranged at the upstream side of the supply port to reduce the flow speed of a teeth whitening fluid supplied to the mouthpieces. This structure is preferable in distribution evenness of the teeth whitening fluid.

The mouthpieces (100; 300; 400) may respectively include occluded elements (120; 310; 420), which inwardly project from the U-shaped outer curved elements (110; 210; 410). This prevents or limits a situation in which the supply port deviates from a predetermined location when using the mouthpiece.

The occluded element (420) may include the internal hollow (402), which is arranged at the upstream side of the supply port to reduce the flow speed of a teeth whitening fluid supplied to the mouthpiece 400. This structure is preferable in distribution evenness of the teeth whitening fluid.

The supply port (403) may open in one or both of the upper surface and the lower surface of the occluded element (420). This allows a teeth whitening fluid to flow from the distal ends of teeth to the basal ends (gums) of the teeth.

The mouthpieces (200; 400) may further include spacer projections (230; 440), which inwardly project from the curved guiding surfaces. This allows a teeth whitening fluid to flow along a passage formed by the spacer projection. This may improve one or both of the guiding efficiency and distribution evenness of the teeth whitening fluid.

The mouthpiece (400) may further include the occluded element (420), which inwardly projects from the U-shaped outer curved element (410). The supply port (403) may open in one or both of the upper and lower surfaces of the occluded element (420), and the spacer projection (440) may oppose the supply port. This allows a teeth whitening fluid discharged from the supply port of the occluded element to flow along a passage formed by the spacer projection. This may improve one or both of the guiding efficiency and distribution evenness of the teeth whitening fluid.

The foregoing description is to be considered as illustrative and not restrictive. For example, the above embodiments or one or more modifications may be used in combination with each other. The subject matter of the present invention may be included in fewer features than all of the disclosed features of the specific embodiments. Accordingly, the claims are incorporated in the detailed description and each claim asserts itself as another embodiment. The scope of the present invention and equivalence of the present invention are to be understood with reference to the appended claims.

DESCRIPTION OF REFERENCE CHARACTERS

10: teeth whitening device
20: coupling portion
30: generator
100: mouthpiece
101: inlet-side passage
102: outlet-side passage
103: supply port
110: outer curved element
111: guiding surface
120: occluded element
121: inner surface
122: outer surface
200: mouthpiece
201: inlet-side passage
202: outlet-side passage
203: supply port
210: outer curved element
211: guiding surface
230: flange
300: mouthpiece
310: occluded element
400: mouthpiece
401: inlet-side passage
402: outlet-side passage
403: supply port
404: teeth rest
410: outer curved element
411: guiding surface
420: occluded element
421: upper surface
422: lower surface
440: flange
G: gum
RU: upper lip
RL: lower lip
TF: front teeth
TR: rear teeth

The invention claimed is:

1. A teeth whitening device comprising:
a generator that generates a teeth whitening fluid which is a gas that contains electrically charged microparticle water;
a mouthpiece having a shape configured to be held by one or more of teeth, gums, and lips of a user to keep the mouthpiece in the mouth of the user so that the user can use the teeth whitening device hands free; and
a coupling portion that couples the generator and the mouthpiece to each other,
wherein the mouthpiece includes a supply port that supplies the teeth whitening fluid generated by the generator into an oral cavity, an inlet-side passage, to which the coupling portion is connected, and an outlet-side passage, which does not include the supply port and guides gas flowing through the inlet-side passage to the supply port,
wherein the generator is configured to generate condensed water by cooling and to atomize the condensed water by generating electric discharging so as to generate the electrically charged microparticle water, which includes radical species serving as teeth-whitening active ingredients, and
wherein the teeth whitening device is configured to cause the gas that contains the electrically charged microparticle water flowing from the generator to the mouthpiece through the coupling portion.

2. The teeth whitening device according to claim 1, wherein the mouthpiece includes an outer curved element that guides the teeth whitening fluid supplied from the supply port into the mouth along the teeth.

3. The teeth whitening device according to claim 1, wherein the mouthpiece includes the supply port formed in a guiding surface that may be opposed to at least either one of upper teeth and lower teeth.

4. The teeth whitening device according to claim 3, wherein the guiding surface includes a portion that may be opposed to a gum, and a flange projecting from the portion that may be opposed to a gum.

5. The teeth whitening device according to claim 1, wherein the mouthpiece includes an occluded element configured to be arranged between upper teeth and lower teeth of a user.

6. The teeth whitening device according to claim 1, wherein the mouthpiece includes an occluded element configured to be arranged between upper teeth and lower teeth of a user, and the outlet-side passage is formed in the occluded element.

7. The teeth whitening device according to claim 6, wherein the supply port is formed in one or both of an upper surface and a lower surface of the occluded element.

8. The teeth whitening device according to claim 1, wherein the outlet-side passage and the inlet-side passage are formed so that a flow speed of teeth whitening fluid flowing through the outlet-side passage is lower than a flow speed of teeth whitening fluid flowing through the inlet-side passage.

9. A teeth whitening device comprising:
a generator that generates a gaseous teeth whitening fluid when activated; and
a mouthpiece connected to the generator in a fluid-communicable manner via a coupling portion that couples the generator and the mouthpiece to each other, the mouthpiece having a shape configured to be held by one or more of teeth, gums, and lips of a user to keep the mouthpiece in the mouth of the user so that the user can use the teeth whitening device hands free,
wherein the mouthpiece includes a U-shaped outer curved element, a supply port that supplies the gaseous teeth whitening fluid, an inlet-side passage, to which the coupling portion is connected, and an outlet-side passage, which does not include the supply port and guides the gaseous teeth whitening fluid flowing through the inlet-side passage to the supply port,
wherein the generator is configured to generate condensed water on an atomization electrode by cooling the atomization electrode and to atomize the condensed water by generating electric discharging through the atomization electrode so as to generate the electrically charged microparticle water, which includes radical species serving as teeth-whitening active ingredients, wherein the gaseous teeth whitening fluid includes the electrically charged microparticle water dispersed in air, and
wherein the teeth whitening device is configured to cause the gaseous teeth whitening fluid flowing from the generator to the mouthpiece through the coupling portion.

10. The teeth whitening device according to claim 9, wherein the outer curved element includes a curved guiding surface configured to guide the teeth whitening fluid discharged from the supply port.

11. The teeth whitening device according to claim 10, wherein the supply port opens in the curved guiding surface.

12. The teeth whitening device according to claim 10, wherein the mouthpiece further includes a spacer projection inwardly projecting from the U-shaped outer curved element.

13. The teeth whitening device according to claim 12, wherein
the mouthpiece further includes an occluded element that inwardly projects from the U-shaped outer curved element,
the supply port opens in one or both of an upper surface and a lower surface of the occluded element, and
the spacer projection opposes the supply port.

14. The teeth whitening device according to claim 9, wherein the outlet-side passage of the mouthpiece includes an internal hollow located at an upstream side of the supply port to reduce a flow speed of the gaseous teeth whitening fluid supplied to the mouthpiece.

15. The teeth whitening device according to claim 9, further comprising an occluded element that inwardly projects from the U-shaped outer curved element.

16. The teeth whitening device according to claim 15, wherein the occluded element includes an internal hollow located at an upstream side of the supply port to reduce a flow speed of the gaseous teeth whitening fluid supplied to the mouthpiece.

17. The teeth whitening device according to claim 15, wherein the supply port opens in one or both of an upper surface and a lower surface of the occluded element.

18. The teeth whitening device according to claim 9, wherein the outlet-side passage and the inlet-side passage are formed so that a flow speed of the gaseous teeth whitening fluid flowing through the outlet-side passage is lower than a flow speed of the gaseous teeth whitening fluid flowing through the inlet-side passage.

* * * * *